United States Patent [19]
Grotendorst

[11] Patent Number: 5,804,176
[45] Date of Patent: Sep. 8, 1998

[54] COMPOSITIONS COMPRISING LEUKOCYTE-DERIVED GROWTH FACTORS AND METHODS OF ADMINISTERING SAME TO FACILITATE WOUND HEALING

[75] Inventor: Gary Robert Grotendorst, Lutz, Fla.

[73] Assignee: The University of South Florida, Tampa, Fla.

[21] Appl. No.: 416,500

[22] Filed: Apr. 4, 1995

Related U.S. Application Data

[63] Continuation of Ser. No. 77,312, Jun. 14, 1993, abandoned, which is a continuation of Ser. No. 472,377, Feb. 1, 1990, abandoned.

[51] Int. Cl.$^6$ .......................... A61K 38/19; A61K 38/18; A61K 38/16
[52] U.S. Cl. ................. 424/85.1; 514/2; 514/8; 514/12; 514/21
[58] Field of Search .............................. 424/85.1; 514/2, 514/8, 12, 21, 886

[56] References Cited

FOREIGN PATENT DOCUMENTS

WO 85/01067  3/1985  WIPO .
WO 90/06321  6/1990  WIPO .

OTHER PUBLICATIONS

Van Brunt. 1989. Bio/Technology 7:15–16.
Abstracts, 20th Annual Meetings, *Journal of Cellular Biochemistry*, Keystone Symposia on Molecular & Cellular Biology, pp. 159, 162, 164, 169, 171, 191 and 197 (1991).
Carrico et al., "Biology of Wound Healing," *Surgical Clinics of North America*, vol. 64, No. 4, pp. 721–733 (1984).
Ford et al., "Characterization of Wound Cytokines in the Sponge Matrix Model," *Arch Surg*, vol. 124, 1422–1428 (1989).
Grotendorst, et al., "Differentiation Production of a Platelet–Derived Growth Factor–Like Mitoattractant by Endoderm Cells Derived from Embryonal Carcinoma Cells," *Journal of Cellular Physiology*, vol. 134, pp. 437–444 (1988).
Jose et al., "Identification of a second neutrophil–chemoattractant cytokine generated during an inflammatory reaction in the rabbit peritoneal cavity in vivo," *Biochem. J.*, vol. 278, pp. 493–497 (1991).
Kapp and Zeck–Kapp, "Activation of the oxidative metabolism in human polymorphonuclear neutrophilic granulocytes: The role of immuno–modulating cytokines," Abstract, 7996000, EMBASE No. 91028645.
Matsuoka and Grotendorst, "Two peptides related to platelet–derived growth factor are present in human wound fluid," *Proc. Natl. Acad. Sci. USA*, vol. 86, pp. 4416–4420 (1989).

Schröder et al., "Identification of a novel platelet–derived neutrophil–chemotactic polypeptide with structural homology to platelet–factor 4," *Biochemical and Biophysical Research Communications*, vol. 172, No. 2, pp. 898–904 (1990).
Schröder et al., "IL–1α or tumor necrosis factor–α stimulate release of three NAP–1/IL–8–related neutrophil chemotactic proteins in human dermal fibroblasts," *The Journal of Immunology*, vol. 144, No. 6, pp. 2223–2232 (1990).
Pencev and Grotendorst, "Human Peripheral Blooc Monocytes Secrete a Unique Form of PDGF," *Oncogene Research*, vol. 3, No. 4, pp. 333–342 (1988).
Schröder et al., "Lipopolysaccharide–stimulated human monocytes secrete, apart from neutrophil–activating peptide 1/interleukin 8, a second neutrophil–activating protein," *J. Exp. Med.*, vol. 171, pp. 1091–1100 (1990).
ten Dijke and Iwata, "Growth Factors for Wound Healing," *Bio/Technology*, vol. 7, pp. 793–798 (1989).
Van Brunt, "Lessons from Wound–healing Clinical Trials," *Bio/Technology*, vol. 7, pp. 15–16 (1989).
Walz et al., "Structure and Neutrophil–activating Properties of a Novel Inflammatory Peptide (ENA–78) with Homology to Interleukin 8," *J. Exp. Med.*, vol. 174, pp. 1355–1362 (1991).
Wenger et al., "Cloning of cDNA Coding for Connective Tissue Activating Peptide III From a Human Platelet–Derived λgtll Expression Library," *Blood*, vol. 73, No. 6, pp. 1498–1503 (1989).
Dyke et al. Bio/Technology vol. 7, 1989, pp. 793–798.
Kapp et al, *J. Invest Dermatol.* 1990, 95(6) Suppl (94–S–95), (abstract only).
Schroder et al, *J. Immounol* 1990, v 144(6) pp. 2223–2232.
Walz et al, *J. Exp. Med.* 1991, v174, pp. 1355–1362.
Jose et al, *Biochem J* 1991, v 298, pp. 493–497.
Schroder et al, Biochem Biophys Res. Comm. v172(2) 1990, pp. 898–904.
Schroder et al. *J. Exp. Med* 1990, v171(3) pp. 1091–1100.
T. Cell. Biochemistry, Keystone Symposium on Wound Repair Apr. 1–7, 1991 various abstracts.
Van Brunt, *Bio/Technology* 7, 1987, pp. 15–16.
Ford et al, *Arch Surg* 124, 1989 pp. 1422–1428.
Carrico et al, Surgical Clin of N. Am. 64(4) 1984, pp. 721–733.

*Primary Examiner*—Elizabeth C. Kemmerer
*Attorney, Agent, or Firm*—Giulio A. DeConti, Jr.; Elizabeth A. Hanley; Lahive & Cockfield

[57] ABSTRACT

A gene encoding a leukocyte-derived growth factor (LDGF) has been isolated, cloned and sequenced. LDGF is believed to correspond to a PDGF-like monocyte-derived growth factor with chemotactic activity which is found in human wound fluid. Protease-resistant and other analogues of LDGF, as well as recombinant LDGF of native amino acid sequence, may now be produced by gene expression in transformed hosts.

13 Claims, 9 Drawing Sheets

```
                      G AGG CAA CTC ACC ATA ACT CAG AGG TCT TCT GGT  34

TCT GGA AAC AAC TCT AGC TCA GCC TTC TCC ACC ATG AGC CTC AGA  70
                                            Met Ser Leu Arg

ATT GAT ACC ACC CCT TCC TGT AAC AGT GCG AGA CCA CTT CAT GCC 124
Leu Asp Thr Thr Pro Ser Cys Asn Ser Ala Arg Pro Leu His Ala

TTG CAG GTG CTG CTG CTT CTG TCA TTG CTG CTG ACT GCT CTG GCT 169
Leu Gln Val Leu Leu Leu Leu Ser Leu Leu Leu Thr Ala Leu Ala

TCC TCC ACC AAA GGA CAA ACT AAG AGA AAC TTG GCG AAA GGC AAA 214
Ser Ser Thr Lys Gly Gln Thr Lys Arg Asn Leu Ala Lys Gly Lys
▲ Platelet Basic Protein              ▲LAPF-4/CTAPIII  ▲ BTG
GAG GAA AGT CTA GAC AGT GAC TTG TAT GCT GAA CTC CGC TGC ATG 259
Glu Glu Ser Leu Asp Ser Asp Leu Tyr Ala Glu Leu Arg Cys Met TGT ATA AAG ACA ACC TCT GGA ATT CAT CCC AAA AAC ATC CAA AGT 304
Cys Ile Lys Thr Thr Ser Gly Ile His Pro Lys Asn Ile Gln Ser TTG GAA GTG ATC GGG AAA GGA ACC CAT TGC AAC CAA GTC GAA GTG 349
Leu Glu Val Ile Gly Lys Gly Thr His Cys Asn Gln Val Glu Val ATA GCC ACA CTG AAG GAT GGG AGG AAA ATC TGC CTG GAC CCA GAT 394
Ile Ala Thr Leu Lys Asp Gly Arg Lys Ile Cys Leu Asp Pro Asp GCT CCC AGA ATC AAG AAA ATT GTA CAG AAA AAA TTG GCA GGT GAT 439
Ala Pro Arg Ile Lys Lys Ile Val Gln Lys Lys Leu Ala Gly Asp GAA TCT GCT GAT TAA TTT GTT CTG TTT CTG CCA AAC TTC TTT AAC 484
Glu Ser Ala Asp ***

TCC CAG GAA GGG TAG AAT TTT GAA ACC TTG ATT TTC TAG AGT TCT 529

CAT TTA TTC AGG ATA CCT ATT CTT ACT GTA TTA AAA TTT GGA TAT 574

GTG TTT CAT TAT GTC TCA AAA ATC ACA TTT TAT TCT GAG GAA GGT 619

TGG TTA AAA GAT GGC AGA AAG AAG ATG AAA ATA AAT AAG CCT GGT 664

TTC AAC CCC TC                                              675
```

*FIG. 1*

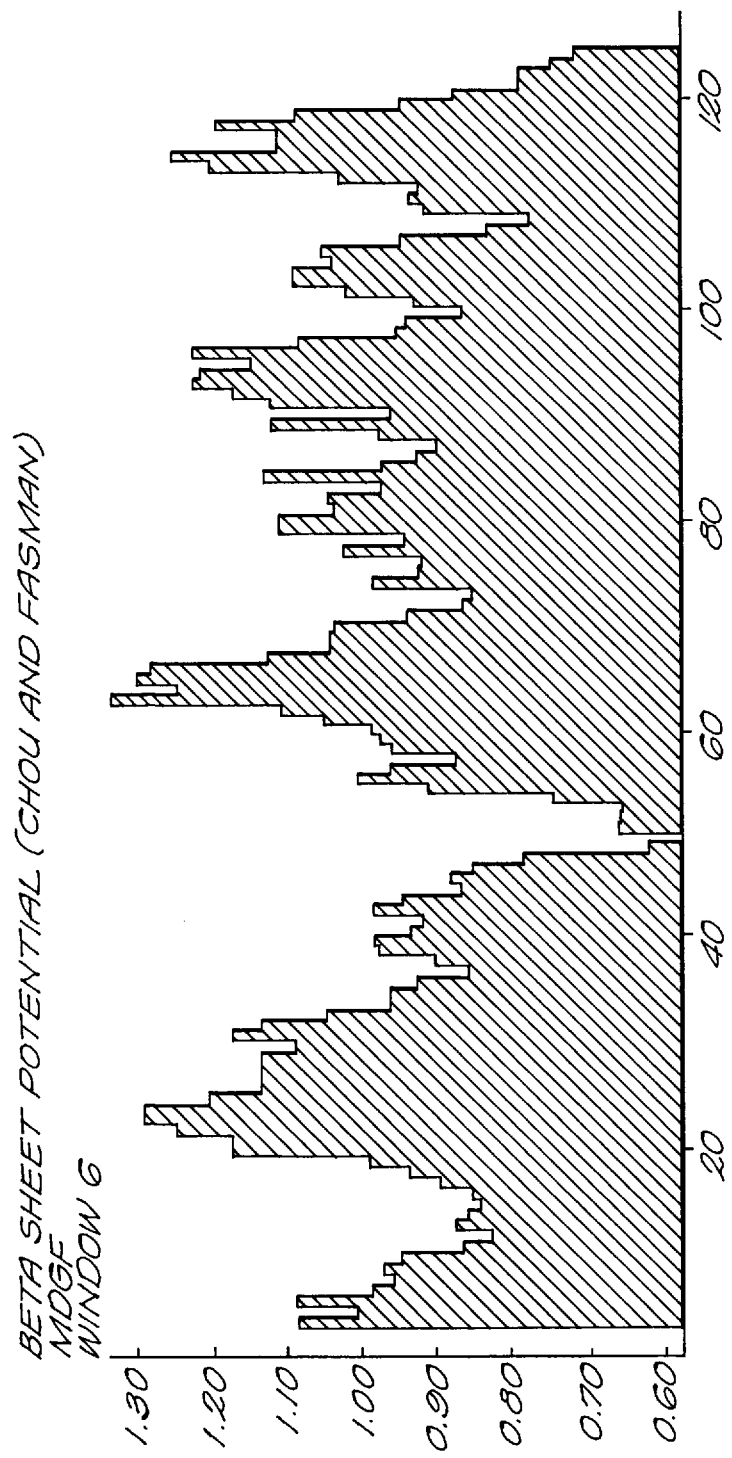

COMPOSITIONS COMPRISING LEUKOCYTE-DERIVED GROWTH FACTORS AND METHODS OF ADMINISTERING SAME TO FACILITATE WOUND HEALING

This application is a continuation of application Ser. No. 08/077,312 filed on Jun. 14, 1993 Entitled: Leukocyte-Derived Growth Factors, now abandoned, which is a continuation of application Ser. No. 07/472,377 filed on Feb. 1, 1990 now abandoned. The contents of all of the aforementioned applications are expressly incorporated by reference.

MENTION OF GOVERNMENT SUPPORT

This invention was made with Government support under Grant #R01 GM-37223 awarded by the National Institutes of Health. The Government has certain rights in the invention.

BACKGROUND OF THE INVENTION

1. Field of the Invention

This invention relates to a leukocyte-derived growth factor which has PDGF-like activity but is structurally distinct from PDGF. This novel growth factor is useful in the healing of wounds. Antibodies against this growth factor are useful in the treatment of fibrotic disorders.

2. Information Disclosure Statement

Within minutes of an injury, platelets adhere to the wound site and aid in clot formation. The phagocytic cells (leukocytes and macrophages) then debride the wound, followed by the connective tissue cells (fibroblasts and smooth muscle-like cells) which proliferate and deposit extracellular matrix. Finally, endothelial cells revascularize the wound site.

Chemotaxis is the directed migration of a cell along a gradient toward the source of a chemical. A chemoattractant is a chemical which specifically stimulates chemotaxis. It is the sequential production of cell type-specific chemoattractants which is responsible for the ordered recruitment of phagocytes, fibroblasts and endothelial cells to the wound site. C5A, platelet factor 4, elastin peptides and certain synthetic N-formylmethionyl peptides attract phagocytes (neutrophils and monocytes). Fibronectin and platelet-derived growth factor summon matrix producing cells. Fibronectin also stimulates endothelial cell migration.

The ability of a cell to respond to a particular factor acting as a chemoattractant is dependent on several biochemical events. First, the attractant molecules must be produced at a site from which they can diffuse into the surrounding tissues and thereby reach the cell in question. Second, the target cell must possess a specific means of detecting small quantities of the chemoattractant (i.e., specific high affinity receptors). Finally, the occupancy of the receptor by the chemoattractant must initate biochemical changes within the cell which activate the cytoskeletal machinery for cell movement.

The proliferation of connective tissues at the wound site is promoted by various polypeptide growth factors. Competence factors (PDGF, fibroblast growth factor, monocyte-derived growth factor) activate quiescent cells in the $G_o$ phase of the cell cycle, enabling them to respond to progression factors. The latter (insulin, somatomedin A or C, alveolar macrophage-derived growth factor) stimulate the cells to enter the S-phase.

PDGF is both a connective cell chemoattractant and a mitogen for such cells, leading to it being termed a "mitoattractant". However, there are other growth factors which have mitogenic action on fibroblasts but are not chemoattractants for them (e.g., epidermal growth factor, transforming growth factors $\alpha$ and $\beta$, somatomedins A and C, and insulin). EGF is a mitoattractant for intestinal epithelial cells.

The extracellular matrix is composed of collagens, glycoproteins and proteoglycans. Cells do not bind directly to collagen but interact via glycoproteins called attachment factors. Such factors include fibronectin, laminin and chondronectin.

Fibrosis is the excessive deposition of connective tissue, largely collagen, in parenchymal tissue, and may be considered "the dark side of wound repair" as it is believed to be the result of an overly prolonged signal for connective tissue repair.

See generally Ross, et al., The Biology of Platelet-Derived Growth Factor, Cell, 46:155–169 (1986); Ross, Platelet-Derived Growth Factor, Ann. Rev. Med., 38:71–79 (1987); Grotendorst, et al., Production of Growth Factors (PDGF & TGFβ) at the Site of Tissue Repair, in GROWTH FACTORS AND OTHER ASPECTS OF WOUND HEALING: BIOLOGICAL AND CLINICAL IMPLICATIONS, pp. 47–54 (1988); Grotendorst, et al., Molecular Mediators of Tissue Repair, in Soft and Hard Tissue Repair; Biological and Clinical Aspects, pp. 20–40 (1984); Grotendorst and Martin, Cell Movements in Wound-Healing and Fibrosis, Rheumatol., 10:385–403 (1986); and Grotendorst, et al., Chemoattractants in Fibrotic Disorders, In Fibrosis, Ciba Foundation Symposium (1985).

Human platelet derived growth factor is a dimeric glycoprotein with a molecular weight of about 30,000 daltons. Nanomolar concentrations of PDGF stimulate replication in 3T3 cells. Reduction of its disulfide bonds destroys PDGF's mitogenic activity. The A- and B- chains of PDGF are related to each other; it is not known whether PDGF is a heterodimer or a mixture of homodimers. The A chain is also heterogeneous, existing in 18 kD, 15 kD, 14 kD and 11 kD forms, while the B chain's only major form is 16 kD. See Johnsson, et al., Biochem. Biophys. Res. Comm., 104:66 (1982). PDGF has been purified to homogeneity, see Heldin, et al., Biochem. J., 193:907 (1981). The cDNA sequence of the PDGF A-chain gene is given in Betsholtz, et al., Nature, 320:695 (1986). The amino acid sequence of both PDGF-1 and PDGF-2 may be found in Doolittle, et al., Science, 221:275 (1983). For expression of PDGF analogues, see Zymogenetics, EP Appln 177,957 (1986). Anti-PDGF antibodies are available, as are antibodies against synthetic peptides derived from the A or B chains (e.g., vs. A92–119 or B79–107). The biological activity of PDGF is reviewed in Ross, Ann. Rev. Med., 38:71 (1987) and Ross, et al., Cell, 46:155 (1986).

There are several aspects of the platelet derived growth factor molecule which may be disadvantageous to its use in the acceleration of wound repair. First, PDGF is a dimeric glycosylated protein which will be more difficult and expensive to produce than smaller non-glycosylated monomeric peptides. Also, there are three isoforms of PDGF which exist (AA, AB, BB). These isoforms exhibit differential biological activity on connective tissue cells and it is not known at present what types and amounts of these are present at sites of tissue repair. However, studies in our laboratory have shown the authentic PDGF peptides are present in only trace amounts in human wound fluid.

An activity of particular interest is PDGF's chemoattractive activity. Grotendorst, Cell, 36:279–85 (1984) observed that cells responsive to PDGF as a mitogen (bovine aortic smooth-muscle cells, human skin fibroblasts, NIH/3T3 cells and NRK cells) also evinced a chemotactic response, while cells for which PDGF was not mitogenic (bovine aortic endothelial cells, MDCK cells, TERA cells, and PAM 212 cells) were not chemoattracted, either. Grotendorst, et al., PNAS (USA), 78:3669 (1981) suggested that the migration of smooth muscle cells from the media to the intima of a blood vessel, which leads to the formation of an atherosclerotic plague may be PDGF-induced.

Connective Tissue Activating Peptide III (CTAP-III), also known as Low Affinity Platelet Factor-4 (LAPF4), is an acid-ethanol stable, slightly basic (isoelectric point 8.5) protein with a molecular weight of about 9,300 daltons, and composed of a single polypeptide chain of 85 residues with a conformation influenced by intrachain disulfide bonds. Castor, et al., Arthritis and Rheumatism, 20:859 (1971); Castor, et al., PNAS (USA), 80:765 (1983); Castor, et al., Biochemistry, 24:1762 (1985); Castor, J. Rheumatol., Suppl. 11:55 (1983). Its amino acid sequence is known, see Castor, et al. (1983), and anti-CTAP III antibodies are available, see Castor (1983). Its biological activities (seen at microgram levels) reportedly include promotion of DNA synthesis, hyaluronic acid synthesis, sulfate incorporation into proteoglycans, prostaglandin $E_2$ synthesis, plasminogen activator secretion, glucose uptake, and lactate formation, see Castor, et al. (1985). Mullenbach, et al., J. Biol. Chem., 261:719 (1986) synthesized a gene which codes for CTAP-III and expressed this protein in yeast. The HPLC-purified recombinant protein was said to exhibit half-maximal mitogenic (stimulation of DNA synthesis) activity at $10^{-7}M$ levels.

The mitogenic activity of CTAP-III (LAPF-4) has been questioned by Holt, et al., Biochemistry, 25:1988 (1986). Holt believes that while the first crude preparations of LA-PF4 tested were mitogenic for 3T3 cells, his more highly purified LA-PF4 was inactive. He remarked, "the purity of the tested material is a crucial issue".

Beta-thromboglobulin (β-TG) is a mitogenically inactive truncated form of CTAP-III. It is missing the N-terminal tetrapeptide of CTAP-III; the remaining 81 residues apparently are not independently active as mitogens. β-TG may, however, be chemotactic. See Holt, et al., Exp. Hematol., 16:302 (1988).

Platelet basic protein (PBP), on the other hand, is CTAP-III with a nine residue N-terminal extension. PBP was initially reported to be a 3T3 cell mitogen at concentrations of 1–10 ng/ml; see Paul, et al., Thrombosis Research, 18:883 (1980). This group later recanted, declaring that purified PBP was free of mitogenic activity. See Holt, et al. (1986). We are not aware of any attempt to express PBP by recombinant DNA techniques.

Shimokado, et al., Cell, 43:277 (1985) fractionated medium conditioned by alveolar macrophages, obtaining fractions with mitogenic activity. An anti-PDGF antibody immunoprecipated a monomeric protein of a molecular weight of 12–13,000 daltons. The protein was not further characterized or purified.

Martinet, et al., Nature, 319:158 (1986) reported that activated human blood monocytes (macrophages) release a substance possessing PDGF-like activity, specifically, chemotactic activity for mesenchymal cells and growth-competence activity for fibroblasts. The substance displaced PDGF from its natural fibroblast receptors and from anti-PDGF antibody. Like PDGF, Martinet's mediator appeared to require disulfide bonding for biological activity.

Pencev and Grotendorst, oncogene Research, 3:333 (1988 issue; actually published in February, 1989) and Matsuoka and Grotendorst, PNAS (USA), 86:4416 (June 1989) relates to work by the inventors, relating to a cheinotactic growth factor. Their work was confined to study of the partially purified native protein.

Collagen, EP Appln 243,179 describes a wound healing composition comprising a growth, chemotactic or differentiation factor.

Urry, U.S. Pat. No. 4,693,718, relates to the stimulation of fibroblast chemotaxis by synthetic peptides corresponding to peptide repeats in tropoelastin.

No admission is made that any reference cited herein is prior art or pertinent prior art. The dates given are the nominal dates appearing in the paper and may not correspond with the publication dates for patent purposes. All references are incorporated by reference to the extent pertinent.

SUMMARY OF THE INVENTION

PDGF is not the principal mitoattractant in human wound fluid. While the fluid reacted with polyclonal anti-human PDGF antibody, the reactive peptides did not correspond well with either PDGF or its subunits. PDGF has a molecular weight of about 30 kDa; the two species of this invention were 16–17 kDa and 34–36 kDa, respectively, and did not comigrate with PDGF. Immunopurified peptides were not recognized by PDGF A- or B- chain specific antisera.

The 16 kDa peptide is believed to correspond with a 16 kDa monomeric chemoattractant secreted by human monocytes and also found to be distinct from PDGF A or B.

Using an anti-PDGF polyclonal antibody as a probe, a cDNA of interest was identified in a cDNA library derived from activated human peripheral blood monocytes. This cDNA encoded a protein which may be described as PBP with a 34 amino acid N-terminal extension. This new peptide is referred to herein as "Leukocyte Derived Growth Factor", (LDGF) since it is secreted by neutrophils as well as monocytes.

This cDNA may be operably linked to a promoter functional in a selected host so that LDGF may be expressed in that host.

The native LDGF acts in a manner which is indistinguishable from that of platelet derived growth factor (PDGF). That is, LDGF is a potent chemotactic and mitogenic factor for connective tissue cells such as fibroblasts, smooth muscle cells and astroglial cells, but not for endothelial cells, epithelial cells or leukocytes. Experimental data suggest that this is due to the interaction of both PDGF and LDGF with the same cell surface receptor molecules. These receptors do not bind other known growth factors including transforming growth factor alpha or beta, epidermal growth factor, insulin-like growth factors, fibroblast growth factors, interleukins, tumor necrosis factor, interferons, or other members of the gro-gene family that have been tested including Platelet factor 4, connective tissue activating peptide III, platelet basic protein, and melanoma growth stimulating activity (gro gene product).

LDGF, and analogues thereof, may be used to facilitate wound healing. In particular, they will be useful in the treatment of many healing impaired conditions including chronic skin ulcers such as decubitis, venous stasis and diabetic ulcers where we find increased levels of this factor compared to normal healing wounds. It would also be useful for the treatment of poor wound healing in surgical wounds where the patients have undergone treatment which impairs healing such as chemotherapy with antineoplastic drugs or steroids. In addition to skin wounds this material would be useful for the treatment of other injuries and surgical procedures where an acceleration of connective tissue formation is desired including bone grafts, bone fracture non-unions, artificial joint replacements, and tendon repairs as we have shown that it is normally present at these sites as well. In the ophthalmic area this material could be very useful for the acceleration of surgical wounds after anterior segment surgery where little bleeding occurs and the wounds heal poorly. Because the material acts in a manner indistinguishable from PDGF and we have demonstrated the efficacy of PDGF in most of the above situations we are certain that this material will provide a suitable stimulation to the same target cells as PDGF acts on.

Because it is smaller than PDGF, contains only a single subunit, and lacks any glycosylation sites so that it is not a glycoprotein as is PDGF, LDGF will be much easier and less expensive to manufacture.

Studies discussed herein have indicated that LDGF is the principal growth factor present in human wounds during the early stages of the repair process. Therefore, addition of this factor more closely mimicks the natural process of wound repair. Use of this factor is less likely to cause unwanted side effects compared to PDGF which is present in much lower amounts at the wound sites.

BRIEF DESCRIPTION OF THE DRAWINGS

FIG. 1 presents the cDNA and translated amino acid sequence for LDGF. Platelet-basic protein, LAPF-4/CTAP-III and β-TG have different N-terminals and a common C-terminal relative to LDGF. The N-termini of these related proteins are marked.

DETAILED DESCRIPTION OF THE PREFERRED EMBODIMENTS

Figure 2A:
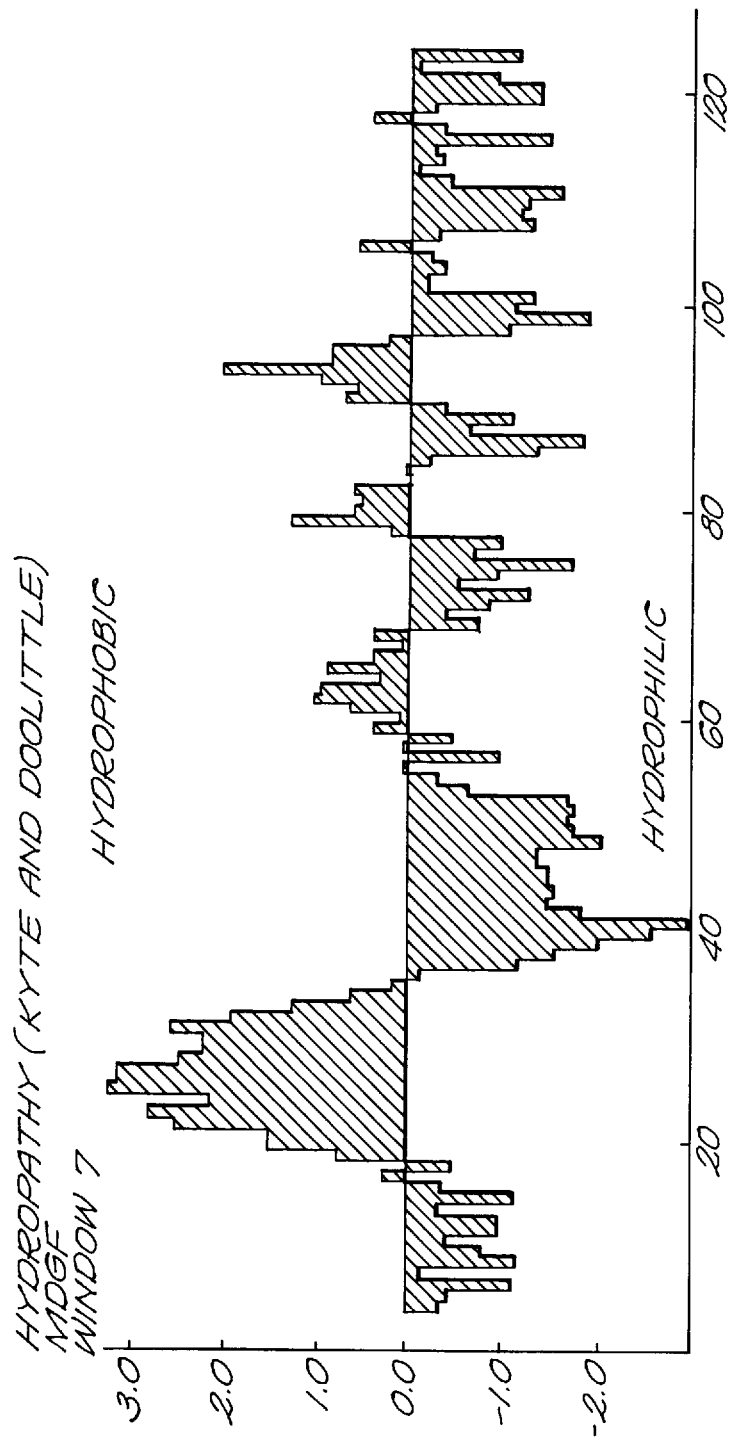
FIGS. 2(A–B) maps the hydrophilic and hydrophobic regions of LDGF by the methods of (A) Kyle and Doolittle, window 7, and (B) Hopp and Woods, window 6. Hydrophilic regions are more likely to lie on the surface and thereby be antigenic.

The present invention relates to a leukocyte-derived growth factor of value in the treatment of wounds. It is believed to induce the chemotaxic movement of connective tissue cells to the wound site and the subsequent proliferation of those cells.

In one aspect, the present invention relates to the purification of a naturally occurring chemotactic and mitogenic factor from media conditioned by activated peripheral blood monocytes or human wound fluid. This factor is characterized as a 16 kD manomeric protein which is recognized by anti-PDGF antibody but not by PDGF A chain- or B chain-specific antibodies, which interacts with the cellular receptor for PDGF, and which differs from PDGF A and B chains in its sensitivity to cyanogen bromide and formic acid. In a preferred embodiment, this factor is partially purified by affinity chromatography on immobilized heparin.

In a second aspect, this invention relates to the discovery that a gene encoding a novel chemotactic factor may be identified by immunoscreening an expression library with anti-PDGF antibodies. This gene or fragments thereof may be used as an oligonucleotide probe to identify and isolate related genes.

In a third aspect, the invention contemplates the cloning and expression of a gene encoding the novel factor LDGF, whose amino acid sequence is given herein and which is believed to be the chemotactic factor purified from monocyte-conditioned media and human wound fluids. Production of LDGF by recombinant techniques is preferred.

In a fourth aspect, the invention relates to the development of novel chemotactic and/or mitogenic factors obtained by expression of a mutagenized LDGF gene or by chemical or enzymatic treatment of the recombinant LDGF protein.

In a fifth aspect, the invention encompasses the preparation of antibodies to LDGF-like proteins, and of the corresponding anti-antibodies which may mimic certain of the properties of LDGF.

LDGF may be obtained by purification from natural sources, e.g., monocyte cell culture supernatants and human wound fluids. However, it is more conveniently obtained synthetically.

Preferably, LDGF is prepared by operably linking a gene encoding the LDGF to a promoter, and expressing the gene under the control of that promoter in a transformed host cell. The gene may be a cDNA as in the Example, or it may be a genomic LDGF sequence (identified using the LDGF-related cDNA as a hybridization probe or anti-PDGF antibody as an immunological probe against a genomic library), or it may be a synthetic DNA (since the LDGF cDNA has been sequenced).

The cell may be a prokaryotic (e.g., bacterial) or a eukaryotic (e.g., yeast, mammalian) cell. The preferred host cells are E. coli. The promoter must be functional in the host cell; a favored promoter is T-7 phage. The LDGF is preferably secreted by the transformed cell; if not, the cell must eventually be lysed so that the LDGF may be recovered.

The LDGF may then be purified to increase its specific activity. Preferably, the LDGF is purified using an anti-PDGF (or LDGF) immunoaffinity column and/or by affinity chromatography on heparin-sepharose.

Purified LDGF may be used to raise polyclonal and monoclonal antibodies against LDGF. These antibodies may be used in the immunopurification of additional LDGF, in assays for LDGF in wound fluid, or in the treatment of fibrotic conditions.

Monitoring the level of LDGF in wound fluid might provide a useful indication of the healing activity at the wound site. The assay is preferably an immunoassay, and is conducted in a competitive or a sandwich format. In one competitive format, sample LDGF competes with labeled LDGF for an insolubilized antibody, which is preferably an anti-LDGF antibody but which could be an anti-PDGF antibody. In one sandwich format, sample LDGF is bound by both an insolubilized antibody and a labeled antibody. The order of introduction of the reactants may be varied.

Antibodies to LDGF may be used to block the LDGF/PDGF receptors and thereby treat fibrotic conditions resulting from overstimulation of the receptors.

While production by recombinant DNA techniques is preferred, the LDGF molecule (or analogues) may also be prepared by concatenation of amino acids or oligopeptides in vitro.

It is believed that analogues of LDGF may share its chemoattractive and mitogenic activity. We believe that the N-terminal extension (relative to PBP) of LDGF substantially enhances its activity and that the three cysteines of LDGF which are aligned with cysteines in the PDGF B chain protein are of special significance. Analogues may be prepared by site-specific mutagenesis (Zoller and Smith, 1984; DNA vol. 3, 479–488) of the LDGF gene and expression of the mutated gene. Preferably, the analogues are substantially homologous with at least the unique "N-terminal extension" of LDGF which distinguishes it from PBP.

It is this region of the LDGF molecule which adds significantly to the sequence homology with the PDGF-B chain including an additional cysteine residue. Also, hydropathy slots of this region of the molecule are very similar to the PDGF-B chain molecule providing further evidence of similar three dimensional structures which would explain the antibody and receptor cross-reactivity. Because we have tested purified CTAP-III, PBP, and β-TG in our biological and immunological tests and found them to be inactive we feel that the additional N-terminal peptide region is essential for PDGF-like biological activity. The term "LDGF-like protein" includes such analogues which substantially contain the N-terminal extension but excludes PDGF, PBP, CTAP-III and β-thromboglobulin. Preferably, the "LDGF-like protein" is more homologous with native LDGF as defined herein than with PDGF, PBP, CTAP-III or β-thromboglobulin. Homology may be determined by the algorithm of Needleman and Winsch, J. Mol. Biol. 48:443–453 (1970) with a window of 100, a gap penalty of 10, a size penalty of 2 and a maximum gap of 50.

These analogues may differ from LDGF by single or multiple insertions, deletions or substitutions. While it is not possible to state with certainty, a priori, what the effect of a given mutation will be, the following generalizations are possible. A mutation is more likely to affect activity if one or more of the following criteria is satisfied:

(1) The mutation affects the 34-AA N-terminal extension which distinguishes LDGF from PBP.

(2) The mutation affects one of the amino acids which is conserved between LDGF and PDGF B chain.

Figure 2B:
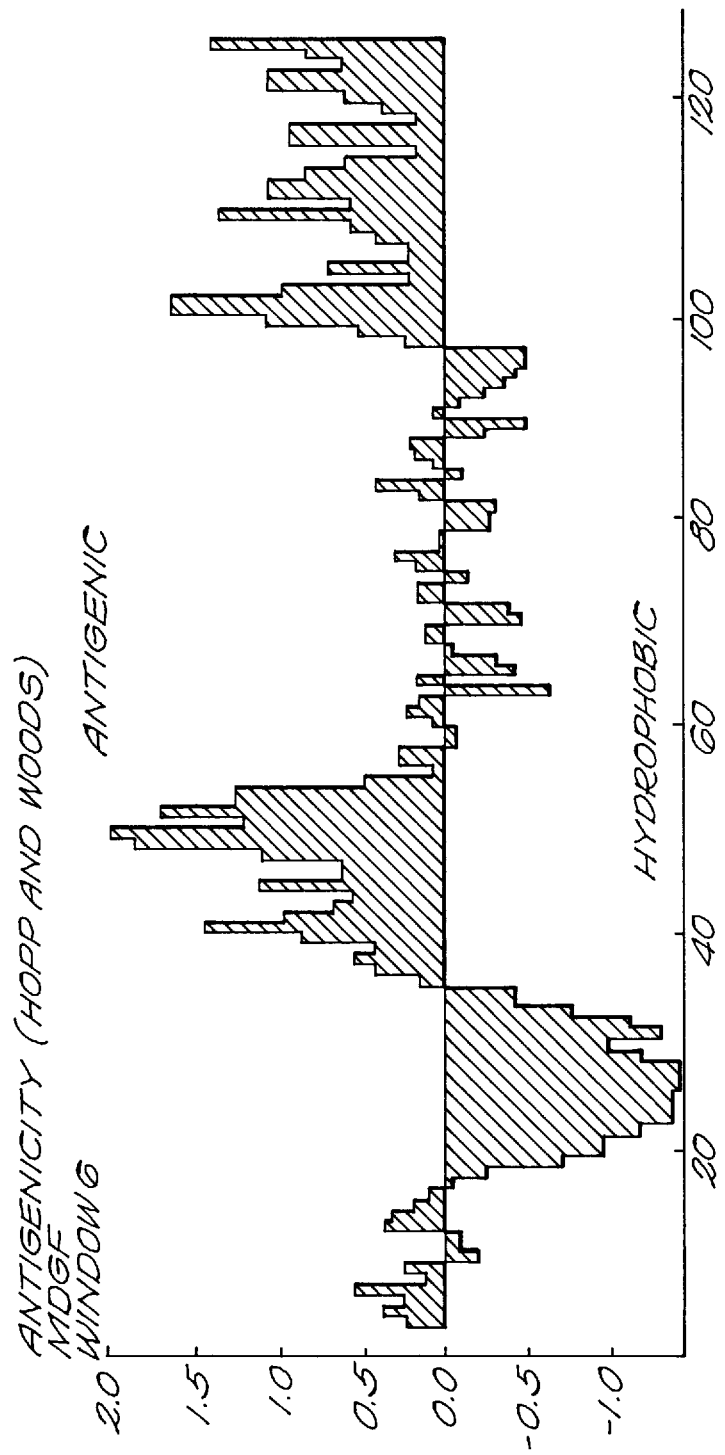

(3) The mutation affects an amino acid which lies in a hydrophilic region of LDGF (see FIG. 2) and which therefore is likely to be exposed to solvent.

Figure 3A:
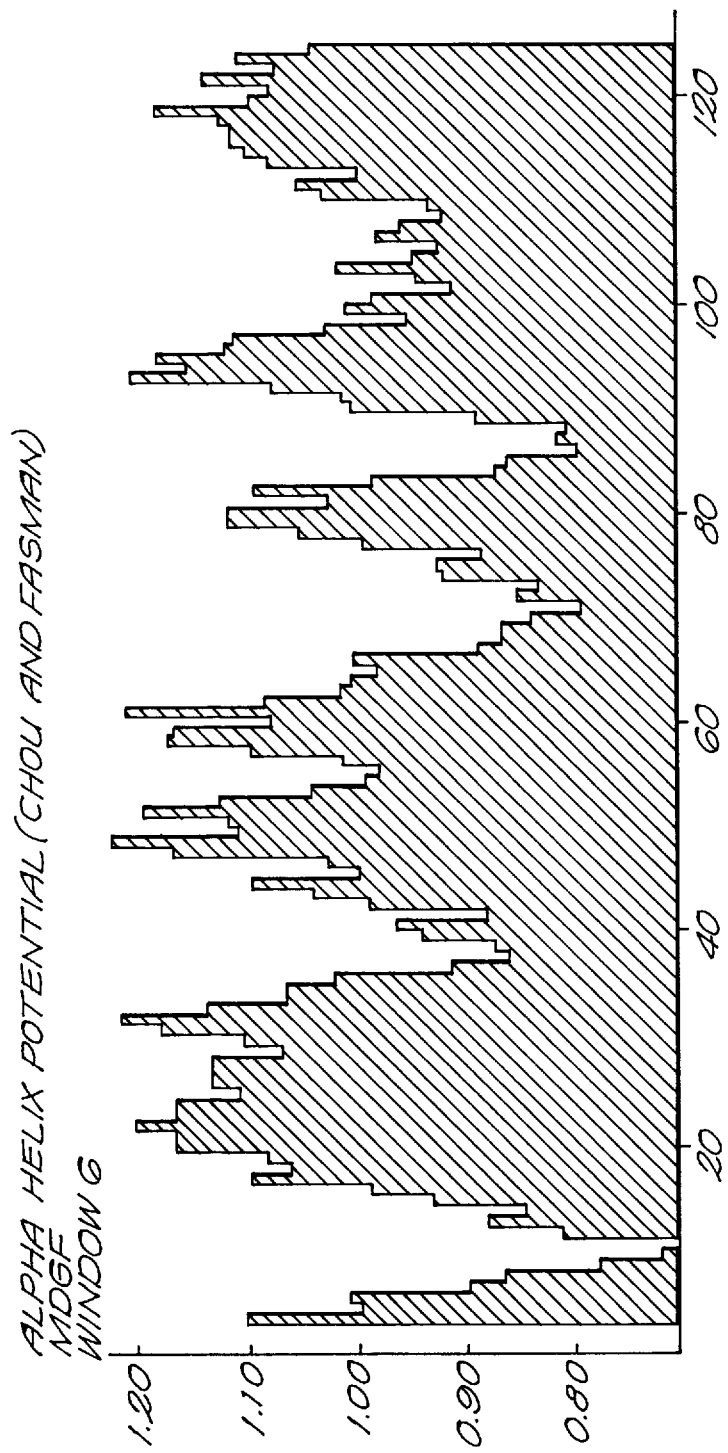
FIGS. 3(A–C) surveys the (A) alpha helix, (B) beta sheet and (C) reverse turn potential across the LDGF sequence, using the algorithm of Chou and Fasman.
Figure 3C:
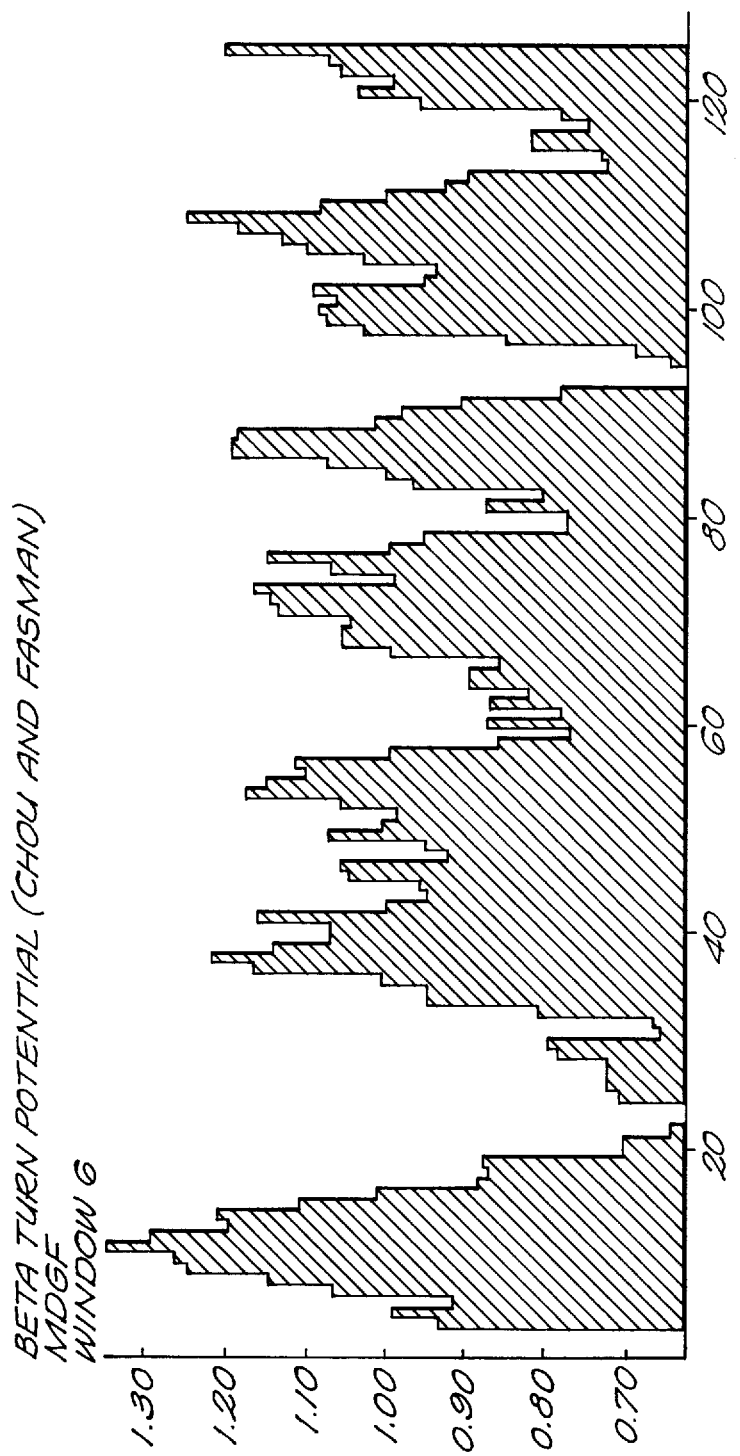
Figure 4:
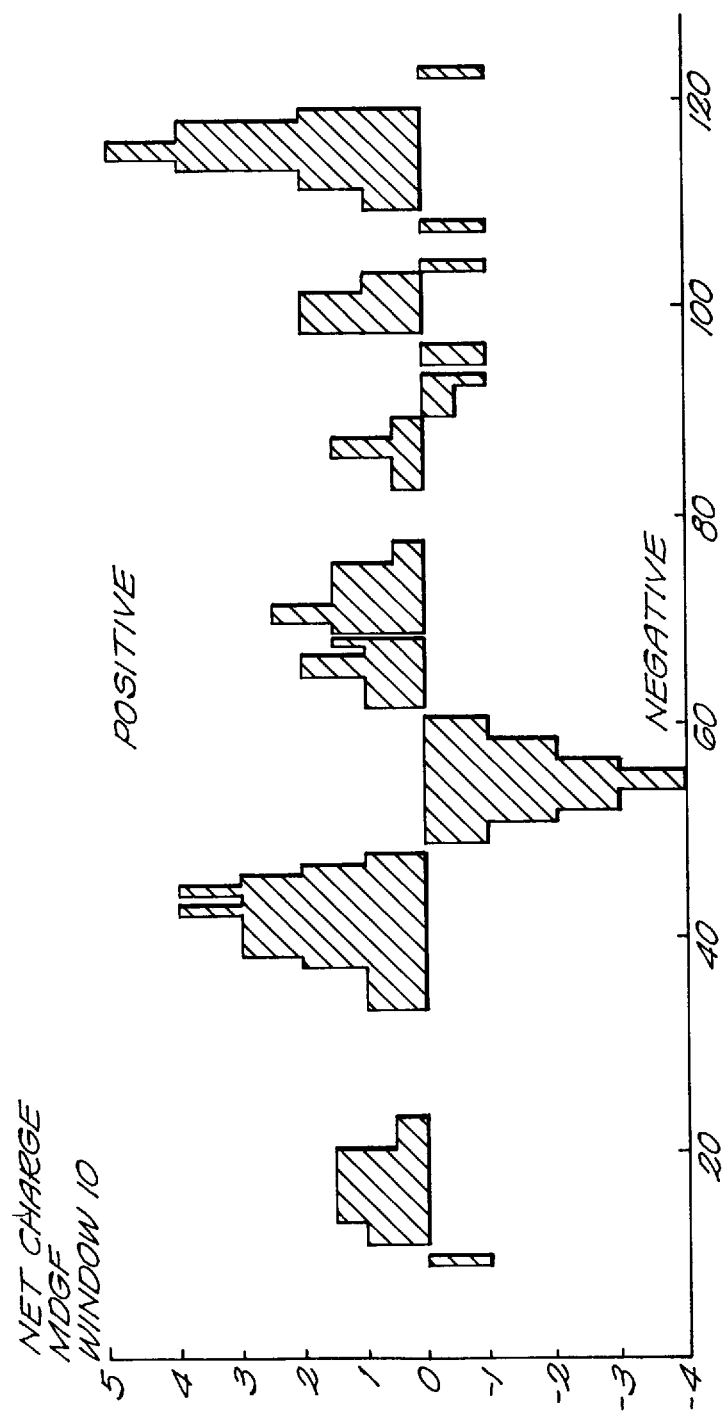
FIG. 4 shows the net charge of LDGF for each window of 10 residues.

(4) The mutation affects an alpha helix or beta sheet region of LDGF as depicted by FIG. 3, particularly if the mutation substantially alters the secondary structure tendency.

Figure 5:
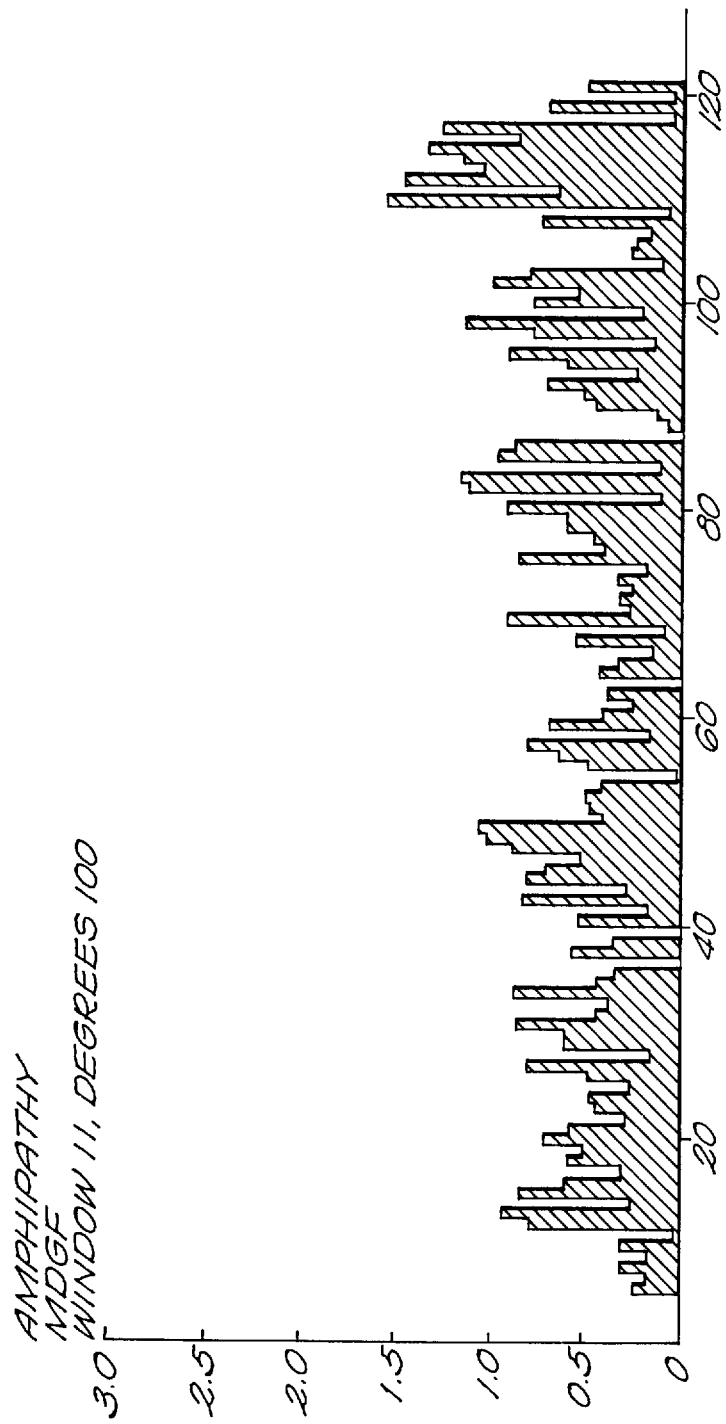
FIG. 5 points out amphipathic alpha-helixes (window 11, degrees 100), which are potential T cell determinants.
Figure 6:
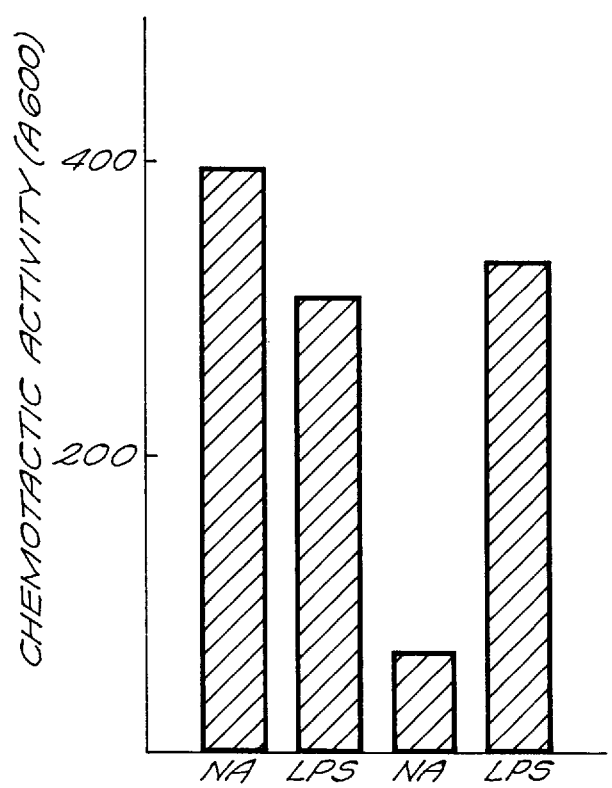
FIG. 6 shows PDGF-like chemotactic activity in media and cell extracts of non-activated and LPS-activated human peripheral blood monocytes.

(5) The mutation substantially increases or decreases the amphipathicity of an amphipathic alpha helix as identified by FIG. 5.

(6) The mutation substantially alters the size of a residue lying in a hydrophobic region of LDGF and therefore thought to be a part of the core of the molecule.

(7) The mutation replaces an amino acid with one of a significantly different structure.

Schultz and Schirmer, *Principles of Protein Structure* 14–16, 170 (1979) analyzed the frequency of amino acid changes between corresponding proteins of homologous organisms. This analysis reveals the existence of exchange groups; amino acids within such a group exchange preferentially with each other. Schultz and Schirmer identify four such exchange groups:

I Phe, Tyr, Trp (aromatic amino acids)

II Lys, Arg, His (positive charged amino acids)

III Val, Leu, Ile, Met, Cys (large aliphatic amino acids)

IV Ser, Thr, Asp, Asn, Gly, Ala, Glu, Gln, Pro (small amino acids)

Schultz and Schirmer also set forth the mutation probabilities for each of the amino acids. Id., 171–172. The amino acids which are replaced most frequently are serine, methionine, and asparagine; the least frequently mutated amino acids are tryptophan, cysteine and tyrosine. Tryptophan has the largest side chain. Cysteine can participate in disulfide bridges. Tyrosine forms very strong hydrogen bonds.

A more stringent definition of conservative substitutions is adopted by the GENEPRO (Riverside Scientific) alignment program, which recognizes the following groups: (Ala, Gly), (Asp, Glu), (Phe, Tyr), (Ile, Leu, Val), (Lys, Arg), (Asn, Gln), and (Ser, Thr).

If a person wishes to substantially alter the biological activity of LDGF (e.g., to obtain LDGF with increased affinity for its cell surface receptor, or to change the balance of the chemotactic and mitogenic activities of LDGF), mutations likely to affect activity according to the above criteria will be introduced. Many of these mutations will abolish rather than enhance activity, of course. One strategy is to randomly mutagenize the LDGF gene (either throughout its length, or focused on residues likely to affect activity) and then screen for functional mutants. Alternatively, candidate mutants may be prepared individually by nonrandom site-specific mutagenesis and then screened.

For an overview of mutagenesis strategies see Botstein and Shortle, Science, 229:1193 (1985). For focused random mutagenesis in particular, see, e.g., Abarzua and Marians, PNAS (USA), 81:2030–34 (1984); Fasano, et al., PNAS (USA), 81:4008–12 (1984); Myers, et al., Science, 229:242 (1985); Matteuci and Heyneker, Nucleic Acids Res., 11:3113 (1983); and Wells, et al., Gene, 34:315–23 (1985).

It may instead be the goal to make only "conservative" mutations in LDGF, that is, changes unlikely to affect activity. The aforementioned criteria are equally useful here. Once again, where there is uncertainty as to the effect of a change, focused random mutagenesis may be employed.

Screening with anti-PDGF (or LDGF) antibodies may also be useful, though immunological activity does not necessarily correlate with biological activity. Analogues may also be screened with PDGF (or LDGF) for ability to competitively inhibit binding to the PDGF (or LDGF) receptor.

It may be advantageous to prepare analogues of LDGF which have increased stability to proteolytic degradation. These analogues would have particular utility in the treatment of chronic wounds where many experts feel that an overproduction of proteases at the site of injury underlies the basis for the impaired healing in these cases, as the proteases degrade the natural growth factors present at the wound site. These analogues would be created by replacing some of the amino acids in the protease cleavage sites which allow for the degradation of LDGF to PBP, CTAP-III and beta-TG, which are inactive forms of the molecule. For example, the two serine residues at position 35 and 36 could be replaced with threonine and the asparagine residue at position 44 could be replaced with glutamine. (Both conservative substitutions by GENEPRO criteria.) Other suitable substitutions could be determined by focused random mutagenesis at these and similar sites.

For techniques not described in detail here but conventional in the molecular biology and immunology arts, see Sambrock, Fritsch and Maniatis, *Molecular Cloning: A*

*Laboratory Manual*, Vols. 1–3 (Cold Spring Harbor: 2d ed. 1989), and Harlow and Lane, *Antibodies: A Laboratory Manual* (Cold Spring Harbor: 1988).

EXAMPLE 1

Characterization of a Monocyte-Derived Growth Factor Isolated from Conditioned Media

MATERIALS AND METHODS

Growth Factors

Human PDGF was isolated from platelets and purified to homogeneity by methods as described previously (Grotendorst, 1984). PDGF A and B chain homodimers were purchased from Biochem, Inc. or from AMGEN, Inc. Pure material as determined by SDS PAGE gel electrophoresis and reverse phase HPLC was used in all biological assays described below and to raise anti-human PDGF antibody.

Antibodies

Purified PDGF or synthetic peptides containing the amino acid terminal sequences of the PDGF A chain (amino acids 92–119 of the precursor molecule) and the PDGF B chain (amino acids 79–107) were used to raise specific antibodies in goats. Goats were immunized with 20 $\mu$g of purified PDGF or 50 $\mu$g of synthetic peptides in Freund's complete adjuvant by multiple intradermal injections. After the fourth rechallenge with 20 $\mu$g of pure PDGF (50 $\mu$g synthetic peptides) in Freund's incomplete adjuvant, immune sera were collected 7 days after the last immunization and tested for specificity by immunoprecipitation and Western blots. The tested immune sera did not show any cross reactivity with other isolated growth factors such as TGF-B (up to 50 ng of pure TGF-B in Western blot analysis) or EGF. Immune sera raised against the PDGF A (92–119) peptide and PDGF B (79–107) peptide proved to be sequence specific as determined by immuno dot blot and did not crossreact with peptides containing remaining amino acid sequences of the PDGF A or PDGF B chain molecule. The IgG fraction of the immune serum was isolated on DEAE Affi gel blue Sepharose (Biorad, Richmond, Calif., equilibrated with 0.02 NaCl, 0.02 Tris pH 8.0).

General Reagents

Lipopolysaccharide (LPS, *E. coli* 0127:B8) was purchased from Sigma Chemical Co., St. Louis, Mo., FMet-Leu-Phe (MLP) from Peninsula Laboratories, San Carlos, Calif., and immune complexes from Cooper Biomedical, Malvern, Pa.

Preparation of LDGF from Human Monocytes and Conditioned Media

Human peripheral blood monocytes were isolated from fresh whole blood using density gradient centrifugation with Hypaque-Ficoll. Adherent cells (>85% monocytes) were cultured in RPMI 1640 medium containing 1 mg/ml bovine serum albumin (BSA) and gentamicin (50 $\mu$g/ml) at a density of $10^6$ cells/ml for 18 hr at 37° C. in an atmosphere of 95% air and 5% $CO_2$ in the absence or the presence of 1 $\mu$g/ml LPS, immune complex (0.5 mg/ml) or fmet-leu-phe ($10^{-6}$M). Conditioned media were removed and the attached cells were scraped in phosphate buffered saline and centrifuged at 2000×g for 10 min. Peptides were extracted from both the media and cell pellets by acid ethanol extraction and ether precipitation as described by Roberts et al. (1980). Briefly 1 vol of conditioned medium or cell pellet from activated or nonactivated cells was extracted with 2 vol of acid/ethanol (1 vol/51 vol) overnight at 4° C. After centrifugation at 600×g for 30 min. the supernatants were precipitated with 4 vol of anhydrous ethyl ether overnight at 4° C. The precipitates were reextracted with 1N acetic acid, lyophilized and tested in smooth muscle cell chemotaxis assay or in Western blots. In some cases conditioned medium was tested either directly for chemotactic activity or lyophilized and resuspended in sample buffer (Tris, SDS, glycerol) and tested in Western blots.

Characterization of LDGF

Partial purification of LDGF from activated monocytes conditioned media was performed by affinity chromatography on heparin Sepharose (Pharmacia, Piscataway, N.J.) eluted with a gradient of 0.1–1N ammonium acetate, pH7 and size exclusion chromatography (HPLC, TSK-2000, developed in 1N acetic acid or 0.5N ammonium acetate).

Partially purified material was further characterized using cyanogen bromide and formic acid digestion as described by Heldin et al. (1986). Aliquots were incubated for 48 hr at 37° C. in 70% formic acid alone or 70% formic acid containing cyanogen bromide (g CNBr/g total protein). Samples were then lyophilized, redissolved in 5 mM HCl and tested for chemotaxis and in Western blots.

Chemotactic activity was measured in the Boyden chamber chemotaxis assay with bovine aortic smooth muscle cells as described previously (Grotendorst et al., 1981, 1982). Samples were tested in duplicates and each result represents mean ±S.D. for 3 experiments. Chemotactic activity is expressed as the milliabsorbance units of stain extracted from the responding cells as described previously in detail (Grotendorst, 1987). Pure human PDGF at a concentration of 6 ng/ml elicits a chemotactic response that gives a value of 350 mAU at $A_{600}$nm. Electrophoresis of each sample was performed on 12 or 15% polyacrylamide gels except for CNBr and formic acid treated material, which was analyzed on 18% gels containing sodium dodecylsulfate (SDS) as described by Laemmli (1970). The proteins were transferred to nitrocellulose by electroblotting as described by Kyhse-Andersen (1984). After transfer the blots were incubated in Tris-buffered saline (TBS) (100 mM NaCl, 50 mM Tris, pH 7.4) containing 2.5 mg/ml nonfat powdered carnation milk (TBS-milk) for 4 hr in order to block nonspecific binding of protein to the filter. The filters we then incubated overnight in the presence of 15 $\mu$g/ml anti-human PDGF IgG diluted in TBS-milk. The filters were then washed 5× in TBS-milk (5 min each) and incubated with alkaline phosphatase conjugated affinity purified rabbit anti-goat IgG (1:1000 dilution) in TBS-milk for 90 min. After washing with TBS-milk (5×) the antigens were detected using an alkaline phosphatase substrate kit (KPL, Gaithersburg, Md.). With this method we can detect as little as 0.3 ng of PDGF in a Western blot.

Non-activated Monocytes Contain PDGF-like Biological and Immunological Activity

Conditioned media from activated peripheral blood monocytes elicited smooth muscle cell chemotaxis in a concentration dependent manner whereas conditioned media collected from nonactivated cells did not contain any detectable level of chemotactic activity. In contrast, cell extracts from both non-activated and activated cells contained approximately equivalent amounts of biological activity suggesting that this material is present within non-activated cells. The concentration of the material secreted was as reported (Martinet et al., 1986) time dependent, reaching a maximal concentration after 18 hr and the response was the same for all the agents used for activation (i.e., LPS, immune complexes). Also as previously reported (Shimokado et al., 1985; Martinet et al., 1986) preincubation of the conditioned media with 30 μg of anti-human PDGF goat IgG completely abolished the biological activity, whereas non-immune goat IgG had no effect on the biological activity of the material.

In order to further characterize the material produced by the peripheral blood monocytes, cell extracts and conditioned media from both non-activated and activated cells were examined by Western blot transfer analysis using anti-human PDGF IgG. Extracts from non-activated monocytes revealed at least five major immunoreactive peptides with distinct molecular weights of 56, 45, 31, 25 and 16 kd. In contrast, the activated monocytes contained only one major immunoreactive peptide of 16 kD identical to the molecular weight of the secreted product from activated cells. Conditioned media from non-activated cells did not contain any detectable immunoreactive material. Preimmune IgG did not react with any peptides in either of the cell extracts or the conditioned media.

Mitogenic Assay for LDGF

NIH/3T3 cells (ATCC CRL1658) were plated in 24 well plates in Dulbecco's Modified Eagle's Medium (DMEM)/10% fetal bovine serum (FBS) at a density of $1 \times 10^4/cm^2$, allowed to grow to confluence and used for assay 3–4 days later. Growth factors were added directly and after 18 hours $^3$H-thymidine (2 uCi/ml) (Amersham, Arlington Heights, Ill.) was added. The cells were incubated an additional 2 hours and washed at 4° C. three times with phosphate buffered saline (PBS), five times with 5% trichloracetic acid (TCA). TCA insoluble materials were solubilized in 0.1N NaOH/0.1% SDS, and the amount of incorporated 3H-Thymidine was determined with a Beckman liquid scintillation counter.

LDGF was purified from activated monocytes in usual manner. PDGF was isolated from platelets as described by Grotendorst, Cell 36:279–285, 1984.

| PDGF | 20 ng/ml | 71,000 cpm | |
|---|---|---|---|
| PDGF | 10 ng/ml | 51,000 cpm | |
| LDGF | 100 ul of sample | 59,000 cpm | ≈14 ng/ml |
| LDGF | 50 ul of sample | 45,000 cpm | ≈7 ng/ml |
| LDGF | 25 ul of sample | 28,000 cpm | ≈3 ng/ml |
| negative control | | 2,500 cpm | |

LDGF is a Monomer Lacking Interchain Disulfide Bridges

Previous studies by several laboratories have suggested that only dimeric forms of PDGF are biologically active (Antoniades et al., 1979; Heldin et al., 1981; Grotendorst et al., 1981). However, the molecular weight of the major immunoreactive peptide secreted by the macrophages as mentioned above was 16 kd as compared to 31 kd for the platelet released PDGF raising the question of the relationship of the monocyte secreted material to PDGF. Western blot analysis of the material secreted by the activated macrophages revealed a doublet of 16 kd on SDS gels. Reduction of these molecules with dithiothreitol did not alter the electrophoretic mobility of the peptides, indicating the absence of interchain disulfide bridges. In marked contrast, electrophoresis on the same gel of authentic human PDGF isolated from platelets exhibits a doublet at 31 kd under nonreducing conditions which shifts after reduction to 18 kd as has been reported previously (Johnsson et al., 1982; Antoniades et al., 1979; Heldin et al., 1981). The molecular weight and relative abundance of the immunoreactive peptides secreted by the monocytes was independent of the agent used to stimulate activation of the cells (LPS, immune complexes, or FMLP; data not shown). These data indicate that under denaturing conditions the major secreted form of LDGF behaves as a monomeric protein of 16 kD on SDS gel electrophoresis.

The molecular weight of this material was examined under non-denaturing conditions. Using gel filtration chromatography on HPLC we compared the elution positions of human PDGF with the monocyte PDGF-like factor (LDGF) on a TSK-2000 column developed in 1N acetic acid or 0.5N ammonium acetate pH 7. Under acidic conditions the elution times of PDGF and the LDGF were nearly identical, indicating that the LDGF behaves as a 30-kd dimer under these conditions. However, the chemotactic activity eluted in 0.5N ammonium acetate as a 18 kD peptide. Western blot analysis of the biologically active fractions demonstrated that the 16-kd immunoreactive peptide co-eluted with the biological activity from this column.

Evidence for the Presence of Additional Methionine Residues in LDGF Compared to PDGF A or B Chain Molecules Human PDGF A and B chain molecules have characteristic primary structures which can be exploited by protein chemical techniques to compare the relationship of the LDGF to these peptides (Heldin et al., 1986). For example, the mature form of the PDGF A chain molecule does not contain any methionine residues (Betsholtz et al., 1986), whereas the mature form of the B chain molecule contains a single methionine at position 11 (Doolittle et al., 1983; Waterfield et al., 1983). In addition the processed A chain contains aspartic acid-proline linkages that are susceptible to cleavage by formic acid digestion. The mature form of the B chain molecule lacks any of these linkages (Doolittle et al., 1983; Waterfield et al., 1983). Thus, B chain molecules are resistant to cleavage with formic acid but are cleaved at position 11 when CNBr is added, resulting in a peptide of reduced molecular weight (Heldin et al., 1986). In contrast, A chain molecules are sensitive to formic acid digestion and CNBr has no additional effect on the fragmentation of A chain peptides (Heldin et al., 1986). LDGF was then treated with either formic acid alone or in the presence of CNBr and both the biological and electrophoretic properties of the treated molecules were analyzed. Formic acid treatment of LDGF under conditions which result in cleavage of the PDGF A chain molecule had no effect on either the biological activity as determined in the smooth muscle cell chemotaxis assay or in the electrophoretic mobility of the major immunoreactive peptide in Western blots. However, CNBr digestion of this material resulted in a complete loss of biological activity as well as completed destruction of the immunoreactive material on Western blots. In contrast, the partially purified PDGF B chain molecule isolated from SSV/NRk cells was easily detected before and after CNBr digestion in the Western blot assay using anti-PDGF IgG.

LDGF is Immunologically Distinct to the Amino Terminals of PDGF A or B Chain

In order to further determine the relation of LDGF to PDGF A or B chain antibody was raised against synthetic peptides containing the N-terminal sequences of the secreted PDGF A (amino acids 92–119) or B (amino acids 79–107) chain. When LDGF was analyzed and compared to reduced PDGF A and B homodimers on Western blots, antibody against the amino terminal peptide of the A chain recognized the reduced PDGF A homodimer but did not react with reduced LDGF or reduced PDGF B homodimer. Antibody against the amino terminal peptide of the B chain immunoreacted with the reduced PDGF B homodimer and did not crossreact with reduced PDGF A homodimer or LDGF (FIG. 5).

Data presented here indicate that activated human peripheral monocytes predominantly secrete only one size class of biologically active peptides of approximate molecular size of 16 kD. These peptides also exhibit smooth muscle cell chemotactic activity, which is completely neutralized by anti-human PDGF antibody. They appear to be processed upon activation entirely within the cells, as extracts of the activated cells contain only peptides with electrophoretic mobility identical to that of the secreted peptides and freshly isolated or non-activated cells contain immunoreactive peptides of larger molecular sizes (54, 45, 31, 25, and 16 kd). Higher molecular weight PDGF related peptides have been described in various cell lines including the simian sarcoma virus transformed marmoset line and are believed to represent precursor forms of the mature molecule that contain additional N and C-terminal amino acids (Robbins et al., 1983). LDGF can exist as a dimer under non-denaturing conditions but lacks any interchain disulfide bridges. This is supported by our observations that LDGF and PDGF coelute on HPLC gel filtration chromatography in acidic condition but exhibit different electrophoretic mobilities on SDS gels. In contrast to PDGF, the mobility of LDGF in the SDS gels is unaffected by the addition of reducing agent. Recent studies by Giese et al. (1987) have shown that modification by site directed mutagenesis of any of the eight conserved cysteine residues in the PDGF-related domain of the v-sis oncogene results in the synthesis of forms of the v-sis gene product (PDGF B chain) that lacks interchain disulfide bridges. However, modification of the cysteine residues at positions 154, 163, 164 and 210 did not alter the transforming activity of the v-sis gene, indicating that certain forms of the v-sis gene product lacking interchain disulfide bridges retain biological activity. Unlike the PDGF A or B chain peptides, the immunoreactivity of the LDGF was completely destroyed by treatment with cyanogen bromide suggesting the presence of additional methionine residues. Also antibody specifically recognizing the amino terminal sequences of the PDGF A and B chain failed to react with LDGF indicating that such amino acid sequences are absent in LDGF, or are significantly altered or not accessible to the antibody, further supporting structural differences between LDGF and PDGF.

In summary, these data suggest that the structure of LDGF is distinct from any of the forms of PDGF which have been characterized to date. This material appears to exhibit all of the PDGF-like biological activities including action as a connective tissue cell chemoattractant and mitogen as well as competition with $[^{125}I]$ PDGF for binding to its cell surface receptor. However, its molecular organization appears to be different from that of the known forms of the PDGF in that it is not an interchain disulfide cross-linked dimer and exhibits different sensitivities to cleavage by formic acid or by CNBr than has been shown for either the processed PDGF A or B chain peptides (Heldin et al., 1986).

The purified material appears to have biological activity at concentrations of 10–40 ng/ml which is at the $10^{-9}M$ range of concentration. This is comparable to the molar concentration of PDGF which are required for similar biological activity.

EXAMPLE 2

Immunodetection of PDGF-Related Peptides in Human Wound Fluid

METHODS AND MATERIALS

Cells. NIH/3T3 cells were obtained in early passage from S. Aaronson (National Institutes of Health). Cells were grown in Dulbecco's modified Eagle's medium (DMEM) supplemented with 10% fetal calf serum and gentamicin (50 µg/ml) and maintained at 37° C. in 90% atmosphere/10% $CO_2$. All mitogenic assays and chemotaxis assays were done by using density-inhibited cultured cells just after they had become confluent.

Human Wound Fluid. Human wound fluids were collected daily from six female patients who had radical mastectomies for tumor (diameter, <1.5 cm) removal. Fluid was collected through the suction tubing placed during surgery for drainage as a customary procedure. None of these patients exhibited any abnormal hematological or cell-mediated immunological variables. Usual postoperative management consisted of drop infusions of antibiotics and vitamins and hemostatic agents such as adrenochrome and tranexamic acids. No anticancer agents were administered during the collection of wound fluids. Wound fluid was separated from tissue debris by centrifugation (10 min at 5000×g) and stored at −20° C.

Growth Factors. Genetically manufactured PDGF AA homodimer, BB homodimer, AB heterodimer, and human epidermal growth factor were supplied by Creative BioMolecules (Hopkinton, Mass.). The concentration and purity were determined by amino acid sequence analysis. Human transforming growth factor type β (TGF-β) was purchased from Research & Diagnostic Systems (Minneapolis, Minn.). Acidic fibroblast growth factor was purchased from Sigma. In some experiments PDGF purified from platelets, as described (Grotendorst, 1984), was used as a standard and immunogen. Macrophage-derived growth factor was purified by HPLC as reported (Pencev and Grotendorst, 1988) from culture supernatant of activated human macrophages.

Antibodies. Anti-human PDGF and anti-synthetic peptide of PDGF A- and B-chain components were used. Goat anti-human PDGF antibody was raised against purified PDGF from platelets (Grotendorst, 1984). This goat anti-PDGF antibody can specifically neutralize the biological activity of PDGF (Grotendorst, et al., 1988).

Anti-A-chain- or anti-B-chain-specific antibodies were prepared by using synthetic peptides containing the amino-terminal sequences of the PDGF A chain (amino acids 92–119) of the precursor molecule) and the PDGF B chain (amino acids 79–107) as immunogens. Immune sera against the PDGF A (92–119) and B (79–107) peptide proved to be sequence specific as determined by immunodot blot and did not crossreact with peptides containing the remaining amino acid sequences of the PDGF A- or PDGF B-chain molecule. Additionally, the antisera are chain specific and react only with the PDGF A- or B-chain peptide, respectively.

Purification of PDGF-Related Peptide in Human Wound Fluid. Due to the high protein concentration the wound-fluid samples or acid-extracted samples cannot be analyzed by Western blot (immunologic) techniques; therefore PDGF-related peptides in human-wound fluid were purified by anti-PDGF immunoaffinity techniques. Goat polyclonal anti-PDGF IgG was conjugated to Affi-Gel-10 (Bio-Rad) as indicated by the manufacturer's protocol. PDGF-related peptides were isolated by incubation of 1 ml of wound fluid, freshly thawed from frozen stock, for 24 hr at 4° C. with 200 µl of Affi-Gel-10 conjugated with anti-PDGF IgG. After incubation with the wound fluid, the matrix was washed five times with 1 ml of 0.1M Hepes, pH 7.4. The specifically bound peptides were released by treatment with 1M acetic acid for 24 hr. The supernatant was then harvested by centrifugation of the matrix and dialyzed against 1.0M acetic acid and stored at −20° C. before assay. Identical amounts of wound fluid and affinity matrix were used to isolate the PDGF-related peptides from each sample. Preliminary studies showed that this amount of affinity matrix is in >10-fold excess for recovering all PDGF-related peptides in the wound-fluid samples. In some experiments human wound fluid was processed by acid ethanol precipitation as described by DeLarco and Todaro (1978).

Western Blot Analysis. Human wound-fluid materials were analyzed by Western blot analysis. Samples were electrophoresed under nonreducing conditions, except in those cases in which anti-peptide antibodies were used in a 15% polyacrylamide gel with SDS, and samples were then electroblotted to nitrocellulose as described (Leibovich and Ross, 1976; Takehara, et al., 1987). Immunoreactive PDGF peptides were detected with anti-human PDGF IgG and alkaline phosphate-conjugated rabbit anti-goat IgG.

Nitogenic and Chemotactic Assays. The mitogenic activity of purified wound-fluid samples was determined as follows. NIH 3T3 cells (Grotendorst, 1984) were cultured in 48-well plates (Costar) in DMEM with 10% fetal calf serum until confluent, and the medium was changed to DMEM with 2.5% fetal calf serum 12 hr before use. Samples in DMEM were added to each well, and DNA synthesis was measured 16 hr later by [$^3$H]thymidine incorporation into trichloroacetic acid-precipitable material.

The chemotactic assays were performed in modified Boyden chambers as described (Grotendorst, 1987) by using collagen-coated polycarbonate filters (Nuclepore; 8-µm-diameter pores). Assays were run for 4 hr in serum-free DMEM containing bovine serum albumin at 2.0 mg/ml. The chemotactic response was quantiated by measuring the absorbance at 600 nm of stain extracted from cells that migrated through the filter.

RESULTS

PDGF-Related Peptide in Human Wound Fluid. Western blot analysis of PDGF-related peptides in human wound fluid revealed two different molecular mass species (16–17 kDa and 34–36 kDa). The Western blot clearly shows that the 16- and 17-kDa peptides are most concentrated in the fluid on the first day after surgery and then decrease by day-7 postsurgery. In contrast, the high-molecular-mass peptides (34–36 kDa) are present in trace quantities at the initial stage of the wound healing process, increase by days 4 and 5, and then decrease by day 7. These findings were essentially the same for each of the six patients whose wound fluid was examined. The 16- to 17-kDa product appears to be derived from macrophages, as it comigrates with a macrophage-derived growth factor (Pencev and Grotendorst, 1988) standard purified from activated macrophages. The 34- to 36-kDa product does not comigrate with PDGF, and we are uncertain of the origin of this peptide.

Specificity of the polyclonal anti-human PDGF is demonstrated by the blocking study of antibody with recombinant human AB PDGF. Preincubation of the first antibody with 50 ng of AB heterodimer completely blocks the binding of that antibody to the PDGF-related peptides in wound fluid. This phenomenon was also seen by using AA or BB homodimers as a blocker. Nonimmune IgG does not detect any peptides in this assay system. Furthermore, this polyclonal anti-human PDGF is specific for PDGF and does not react with TGF-β (100 ng), human epidermal growth factor (100 ng), or acidic fibroblastic growth factor (100 ng). The wound fluid was red in color during the first 3 days of collection, indicating that bleeding and coagulation occurred at the wounding site. Surprisingly, in spite of the platelet activation occurring at the site, we could not detect any authentic 30-kDa PDGF in any sample from the six sets of wound-fluid samples examined.

Efficacy of Anti-PDGF Immunoaffinity Purification. Several explanations for the inability to recover authentic 30-kDa PDGF are (i) 30-kDa PDGF has been degraded by enzymatic digestion, (ii) the immunoaffinity-purification procedure is not effective enough to pick up the antigen from the protein-rich wound fluid, or (iii) 30-kDa PDGF is bound to carrier proteins and is therefore inaccessible to the antibody. To address these questions, a known amount of PDGF (20 ng/ml) was added into the wound fluid. The sample was incubated for 24 hr at room temperature, and the PDGF-related peptide was purified by the aforementioned immunoaffinity procedure. Recovery of the exogenously added PDGF was >90%, and the amount of immunoreactive peptides present in the wound fluid did not differ with or without addition of authentic PDGF. These results strongly argue that any PDGF present in the wound fluid would be recoverable with this isolation procedure and that the amount of matrix used is in excess, as doubling the amount of PDGF antigen in the fluid sample had no effect on recovery of PDGF or PDGF-related peptides as judged by the Western blot assay.

Absence of PDGF A- and B-Chain Peptides in Human Wound Fluid. To examine whether the PDGF-related peptide in the wound fluid was composed of PDGF A or B chains larger amounts of purified PDGF-related peptides from day-1 wound fluid were analyzed using antisera specific for the PDGF A or B chain. These sera were produced against 30-mer synthetic peptides that correspond to the N-terminal sequence of either the mature A- or B- chain molecule. These antisera are chain specific and can detect as little as 1 to 2 ng of either the intact A- or B-chain peptide. Neither antisera detected any A- or B-chain peptides in a sample of day-1 wound fluid that contained the equivalent of 20 ng of PDGF biological activity. These results suggest that PDGF A- or B-chain peptides must be present in concentrations of <2 ng/ml in the wound fluid and that the principal PDGF-related biological activity cannot be attributed to A- or B-chain molecules in the wound fluid.

Biological Activity of PDGF-Related Peptide in Human Wound Fluid. The amount of PDGF-related peptides was determined by using both densitometric scanning of the Western peptide blots and biological assays. The kinetics of appearance and disappearance of the 16- to 17-kDa and 34- to 36-kDa product were independent of each other. The level of the 16- to 17-kDa peptide peaked on the first day after surgery and decreased exponentially to nearly undetectable levels by the seventh day. In contrast, the 34- to 36-kDa product was initially present at low levels and then increased, reaching peak levels on the fifth and sixth days postsurgery.

The chemotactic and mitogenic activity of the total wound fluid and immunoabsorbed fraction was investigated. The mitogenic activity of the immunoaffinity-purified fraction was highest on day 1 and decreased to undetectable levels after the fourth day postsurgery. These kinetics are identical to that of the 16- to 17-kDa peptide as detected in the Western blot analysis. The mitogenic activity of the total wound fluid differed from that of the immunoaffinity-purified fraction; this activity peaked on the fifth day, at which time the total mitogenic activity was greater than that of immunoaffinity-purified material. Thus, multiple mitogenic activities are present in the wound fluid, only some of which immunologically relate to PDGF.

The chemotactic activity of the total wound fluid and the immunoaffinity-purified fraction was also investigated. As for mitogenic activity, the amount of chemotactic activity in the immunoaffinity-purified fraction correlated with the day-to-day change of the 16- to 17-kDa peptide as measured by Western blot analysis. This activity peaked on the first day and then decreased.

Chemotactic activity of the purified PDGF-related peptides from wound fluid was treated with recombinant PDGF in a competitive assay (Table 1). PDGF-related peptides from day-1 wound fluid elicited a strong chemotactic response by NIH 3T3 cells without recombinant PDGF BB homodimer in the upper chamber. However, when PDGF BB homodimer at 25 ng/ml was added to the upper chamber, decreasing the concentration gradient of chemoattractant, no cells migrated toward the lower chamber in response to the immunopurified factor. These data indicated that the immunopurified chemotactic factor is probably acting through the PDGF receptor.

The activity present in acid ethanol extracts of wound fluid-exhibited kinetics different from those of the immunoaffinity-purified PDGF-related peptides, as the activity was at its peak on the fourth day of postsurgery. Thus, as with the mitogenic activity, multiple chemotactic activities appear to be present, some that are PDGF like and others that are not.

The PDGF-related chemotactic and mitogenic activities appear to be primarily mediated by a factor that resembles a macrophage-derived PDGF-related peptide and not authentic platelet PDGF (Pencev and Grotendorst, 1988). Whether this factor is exclusively produced by macrophages is not yet clear. Recent work in my laboratory indicates neutrophils can produce a similar factor, although at present the relationship of this factor with macrophage-derived growth factor is unknown. Nonetheless, macrophages have long been felt to play a central role in controlling the wound repair response (Leibovitch and Ross, 1975; Diegelmann, et al., 1980), and it is not unexpected to find abundant levels of an apparent macrophage-related product in the wound fluid. The absence of any authentic PDGF peptides in the wound fluid was surprising; whether these peptides are present in amounts below assay sensitivities or only present in trace quantities is unclear. If authentic PDGF peptides are present in low levels in the wound fluid, they must account for <10% of the total PDGF-related biological activity. That the authentic PDGF is masked in some manner or is degraded during the aforementioned isolation procedures is unlikely, as added PDGF is recovered with >90% efficiency from the wound-fluid samples. Possibly the PDGF A- and B-chain peptides are predominantly associated with the extracellular matrix or fibrin clot and are therefore not,free in solution. Alternatively, the authentic PDGF could be rapidly consumed at the site of tissue repair by tissue elements.

A significant portion of the chemotactic and mitogenic activities in the wound fluid collected during the later stages of the repair response remained after depletion of the PDGF-related peptides by immunoabsorption. The mitogenic and chemotactic activities in untreated wound fluid or acid ethanol extracts, which resemble each other, exhibit different time courses of appearance than those of the immunoaffinity-purified materials. These activities reach peak levels on later days, when the level of 16- to 17-kDa PDGF-related peptide has decreased, indicating that these factors are probably produced by different cell types than those producing the PDGF-related peptides. Thus, mitogenic and chemotactic factors distinct from PDGF are also present in wound fluid and may play essential roles in regulating later stages of the repair process.

These results show the presence of PDGF-related peptides at sites of normal wound healing in humans. Similar peptides have been found in both ascites fluid and liver biopsy tissue obtained from individuals with chronic alcoholic cirrhosis. Because this disorder is characterized by chronic inflammation of the liver and a large accumulation of mononuclear cells at this site, macrophage-derived growth factor is a probable component of the initiation of fibrotic diseases as well. Thus, it appears that cell types, such as macrophages, may figure importantly in the production of PDGF-related growth factors during the normal repair and regeneration of tissue after traumatic injury and that similar factors may stimulate connective-tissue formation during fibrotic disorders such as atherosclerosis, arthritis, pulmonary fibrosis, and liver cirrhosis.

EXAMPLE 3

Isolation and Characterization of LDGF-Related CDNA

Total RNA from activated (LPS treated [1/ug/ml] 24 hours) human peripheral blood monocytes was prepared by the method of Chugauin et al.; (Biochemistry; 18:5294–5299; 1979). The poly A+ containing mRNA was isolated by oligo dt cellulose chromatography. A cDNA copy of all the mRNAs present was constructed using a cDNA library construction kit purchased from Pharmacia. The cDNAs were then blunt ended and had EcoR1 adaptors added to the ends. The cDNAs were isolated by low melt agarose electrophoresis and all of the cDNA's larger than 800 base pairs in length were collected by low melt agarose electrophoresis and packaged into a lambda gt 11 expression vector. This genetic vector packages the cDNA insert in a position so that it is under the control of a beta galactosidase promoter and when the appropriate stimulus is added to the bacterial culture media this promoter activates the synthesis of a fusion protein which contains a N-terminal of beta-galactosidase and the C-terminal of the protein sequence encoded by the cDNA packaged into that phage genome. only a single cDNA sequence is packaged per phage genome.

The expression library was then screened with the anti-PDGF antibody we had prepared in goats and used to identify LDGF in the conditioned media. A total of 800,000 recombinant phage were screened and a single phage produced a fusion protein which reacted with the antibody. This phage was plaque purified and the insert cut out using Eco R1 restriction endonuclease. It was evident from our restriction fragments that the insert contained an internal EcoR1 site at approximately 300 bases in from one of the EcoR1 linkers.

The intact insert was then subcloned in M13 using partial digestion with EcoR1 and screening a large number of recombinants for the intact insert. Several plaques were picked for single strand DNA sequencing using the Dideoxy method. DNA sequence analysis revealed an insert of 675 base pairs which contained a single open reading frame of 384 bases (FIG. 1) and the predicted internal EcorR1 site. A search of the Genbank library with this sequence revealed that this was a unique sequence and showed a 40% homology to the protein encoded by the gro gene (see Table 2). This indicated that the cDNA was related to the CTAP-III gene family. The open reading frame was translated using the PC-GENE program and compared with protein sequences in the data base. The protein sequence showed regions of identity with three known proteins, Platelet-basic protein (PBP), CTAP III or LA-PF4, and beta-thromboglobulin (βTG). However, the predicted LDGF sequence contained an additional 34 amino acids at the N-terminal of the PBP-related sequence. CTAP-III and βTG are believed to be proteolytic breakdown products of PBP. In fact beta-thromboglobulin is used as a marker for outdating platelets. In our tests neither PBP, LA-PF4, or βTG displayed any biological or immunological activity. Thus, it appears that the additional amino acids present in the N-terminal of the LDGF protein are essential for its biological activity. Using microcomputer programs (GENEPRO, Riverside Scientific), it has been shown that there is a 25% homology between LDGF and regions of the PDGF B chain molecule if one includes substitutions of certain amino acids which are neutral to the molecular structure. (see Table 3). Importantly, 3 of the 5 cysteine residues in the LDGF sequences are aligned with cysteines in the PDGF B chain protein. Furthermore, comparison of hydropathy slots which reflect the hydrophobic and hydrophilic regions of LDGF and PDGF-B chain indicate that the intact LDGF molecule has a very similar profile as seen in PDGF. These similarities may explain the basis for the antibody and receptor binding cross reactivity, and suggests there are loops of the molecule which may share regions of structural identity.

LDGF is produced by both activated macrophages and neutrophils. Furthermore, when fluid collected from healing surgical wounds in humans was analyzed it was found that LDGF was the principal PDGF-like factor in the wound fluid and authentic PDGF was absent (Example 2). LDGF is present in all types of normal healing wounds including skin wounds and orthopedic surgical wounds (bone fusion).

Importantly, wound fluid collected from non-healing skin ulcers which occur in diabetic patients, steroid treated rheumatoid patients and individuals who have peripheral circulatory problems has been analyzed and, in all cases examined to date, neither PDGF-like biological activity nor LDGF immunoreactivity has been detected in these samples using equivalent amounts as those tested from the normal healing individuals. These results implicate a deficiency of LDGF at sites of injury in individuals with healing impairments. This material was also present in liver tissue of patients with chronic alcoholic cirrhosis but not in normal liver tissue or tissue from diseased livers which do not develop fibrotic complications such as hepatoma.

REFERENCES

Antoniades, H. N., Scher, C. D., and Stiles, C. D. (1979). Purification of human platelet derived growth factor. Proc. Natl. Acad. Sci. (USA), 76 1809–1813.

Baird, A., Mornede, P., and Bohlen, P. (1985). Immunoreactive fibroblast growth factor in cells of peritoneal exudate suggests its identity with macrophage derived growth factor. Biochem. Biophys. Res. Commun., 126, 358–364.

Barret, T. B., Gajdusek, C. M., Schwartz, S. M., McDougall, J. K. & Benditt, E. P. (1984) Proc. Natl. Acad. Sci. (USA), 81, 6772–6774.

Betsholtz, C., Johnsson, A., Heldin, C. H., Westermark, B., Lind, P., Urdea, M. S., Eddy, R., Shows, T. B., Philpott, K., Mellor, A. L., Knott, T. J., and Scott, J. (1986). cDNA sequence and chromosomal localization of human platelet derived growth factor A-chain and its expression in tumor cell lines. Nature, 320, 695–699.

Bittermann, P. B., Rennard, S. I., Hunninghake, G. W., and Crystal, R. G. (1982). Human alveolar macrophage growth factor for fibroblasts: regulation and partial characterization. J. Clin. Invest., 70, 806–822.

Collins, T., Bonthron, D. T., and Orkin, S. H. (1987). Alternative RNA splicing affects function of encoded platelet-derived growth factor A-chain. Nature, 328, 621–624.

DeLarco, J. E. & Todaro, G. J. (1978) Proc. Natl. Acad. Sci. (USA), 75, 4001–4005.

DeLustro, F., Sherer, S. K., and LeRoy, E. C. (1980). Human monocyte stimulation of fibroblast growth by a soluble mediator(s). J. Reticuloendoethel. Soc., 28: 519–532.

Diegelmann, R. E., Cohen, I. K. & Kaplan, A. M. (1980) Plastic Reconstr. Surg., 68, 107–113.

Doolittle, R. F., Hunkapiller, M. W., Hood, L. E., Devare, S. G., Robbins, K. C., Aaronson, S. A., and Antoniades, H. N. (1983). Simian sarcoma virus onc gene, v-sis, is derived from the gene (or genes) encoding a platelet derived growth factor. Science, 221, 275–277.

Douglass, J., Cirelli, O., and Herbert, D. (1984). Protein gene expression: generation of diversity of neuroendocrine peptides, Annu. Rev. Biochem., 53, 665–671.

Estes, J. E., Pledger, W. J., and Gillespie, G. Y. (1984). Macrophage-derived growth factor and interleukin 1 are distinct entities. J. Leuk. Biol., 35, 115–129.

Giese, N. A., Robbins, K. C., and Aaronson, S. A. (1987). The role of individual cysteines residues in the structure and function of the v-sis gene product. Science, 236, 1315–1318.

Glenn, K., and Ross, R. (1981). Human monocyte-derived growth factor(s) for mesenchymal cells: activiation of secretion by endotoxin and concavalin A. Cell, 25, 603–615.

Grotendorst, G. R., Pencev, D., Martin, G. R. & Sodek, Jr. (1984) in Soft and Hard Tissue Repair, eds. Hunt, T. K., Heppenstall, R. B., Pines E. & Rovee, D. (Praeger, N.Y.), pp. 20–44.

Grotendorst, G. R. (1984). Alteration of the chemotactic response of NIH/3T3 cells to PDGF by growth factors, transformation and tumor promoters. Cell, 36, 279–285.

Grotendorst, G. R. (1987). Spectrophotometric assay for the quantitation of cell migration in the Boyden chamber chemotaxis assay. Methods Enzymol., 147, 144–152.

Grotendorst, G. R., Harvey, A. K., Nagarajan, L., Anderson, W. B. & Gatewood, E. (1988) J. Cell Physiol., 134, 437–444.

Grotendorst, G. R., Seppa, H. E., Kleinman, H. K., and Martin, G. R. (1981). Attachment of smooth muscle cells to collagen and their migration toward platelet derived growth factor. Proc. Natl. Acd. Sci. (USA), 78, 3669–3672.

Grotendorst, G. R., Chang, T., Seppa, H. E., Kleinman, H. K., and Martin, G. R. (1982). Platelet derived growth factor is a chemoattractant for vascular smooth muscle cells. J. Cell Physiol., 113, 261–266.

Grotendorst, G. R., Seppa, H. E., Kleinmann, H. K. & Martin, G. R. (1981) Proc. Natl. Acad. Sci. (USA), 78, 3669–3672.

Heldin, C. H., Westermark, B., and Wasteson, A. (1981). Platelet-derived growth factor: isolation by a large scale procedure and analysis of subunit composition. Biochem. J., 193, 907–913.

Heldin, C. H., Johnsson, A., Wennegren, S., Wernstedt, C., Betsholtz, C., and Westermark B. (1986). A human osteosarcoma cell line secretes a growth factor structurally related to a homodimer of PDGF A-chains. Nature, 319, 511–514.

Johnsson, A., Heldin, Ch. H., Westermark, B., and Wasteson, A. (1982). Platelet derived growth factor: identification of constituent polypeptide chains. Biochem. Biophys. Res. Commun., 104, 66–74.

Kyhse-Andersen, J. (1984). Electroblotting of multiple gels: a single apparatus without buffer tank for rapid transfer of proteins from polyacrylamide to nitrocellulose. J. Biochem. Biophys. Methods, 10, 203–209.

Laemmli, U. K. (1970). Cleavage of structural proteins during the assembly of the head of bacteriophage T4. Nature, 227, 680–685.

Lawrence W. T., Sporn, M. B., Gorshboth, C., Norton, J. A. & Grotendorst, G. R. (1986) Ann. Surg. 203, 142–147.

Leibovich, S. J. & Ross, R. (1975) Am. J. Pathol., 84, 71–100.

Leibovich, S. J., and Ross, R. (1976). A macrophage dependent factor that stimulates the proliferation of fibroblasts in vitro. Am. J. Pathol., 84, 501–554.

Martinet, Y., Bitterman, P. B., Mornex, J.-F, Grotendorst, G. R., Martin, G. R. & Crystal, R. G. (1986). Activated human monocytes express the c-sis proto-oncogene and release a mediator showing PDGF-like activity. Nature (London), 319, 158–160.

Mornex, J.-F., Martinet, Y. Yamauchi, K., Bitterman, P. B., Grotendorst, G. R., Chytil-Weir, A., Martin, G. R., and Crystal, R. G. (1986). Spontaneous expression of the c-sis gene and release of a platelet derived growth factorlike molecule by human alveolar macrophages. J. Clin. Invest., 78, 61–66.

Pencev, D. & Grotendorst, G. R. (1988) Oncogene Res., 3, 333–342.

Pledger, W. J., Stiles, C. D., Antoniades, H. N. & Scher, C. D. (1977) Proc. Natl. Acad. Sci. (USA), 74, 4481–4485.

Roberts, A. B., Lamb, L. C., Newton, D. L., Sporn, M. B., DeLarco, J. E., and Todaro, G. J. (1980). Transforming growth factors: isolation of polypeptides from virally and chemically transformed cells by acid/ethanol extraction. Proc. Natl. Acad. Sci. (USA), 77 3494–3498.

Robbins, K. C., Antoniades, H. N., Devare, S. G., Hunkapiller, M. W., and Aaronson, S. A. (1983). Structural and immunological similarities between simian sarcoma virus gene products and human platelet derived growth factor. Nature, 305, 605–608.

Ross, R. & Benditt, E. P. (1961) J. Biophys. Biochem. Cytol., 11, 665–677.

Schmidt, J. A., Mizel, S. B., Cohen, D., and Green I. (1982). Interleukin 1, a potential regulator of fibroblast proliferation. J. Immunol., 128, 2177–2182.

Seppa, H. E., Grotendorst, G. R., Seppa, S., Schiffmann, E. & Martin, G. R. (1982) J. Cell Biol., 92, 584–588.

Shimokado, K., Raines, E. W., Madtes, D. K., Barrett, T. B., Benditt, E. P., and Ross, R. (1985). A significant part of macrophage-derived growth factor consists of at least two forms of PDGF. Cell, 43, 277–286.

Takehara, K., Grotendorst, G. R., Silver, R. & Leroy, E. C. (1987) Arteriosclerosis, 7, 152–158.

Tong, B. D., Auer, D. E., Jaye, M. Kaplow, J. M., Ricca, G., McConathy, E., Drohan, W., and Deuel, T. F. (1987). cDNA clones reveal differences between human glial and endothelial cell platelet derived growth factor A-chains. Nature, 328, 619–621.

Tsukamoto, Y., Helsel, W. E., and Wahl, S. M. (1982). Macrophage production of fibronectin, a chemoattractant for fibroblasts. J. Immunol., 127, 673–678.

Vogel, A. E., Raines, E., Kariya, B., Rivest, M.-J. & Ross, R. (1978) Proc. Natl. Acad. Sci. (USA), 75, 2810–2814.

Waterfield, M. D., Scrace, G. T., Whittle, N., Stroobant, P., Johnsson, A., Wasteson, A., Westermark, B., Heldin, C. H., Huang, J. S., and Deuel, T. F. (1983). Platelet-derived growth factor is structurally related to the putative transforming protein p28sis of simian sacroma virus. Nature, 304, 35–39.

TABLE 1

BLOCKING OF CHEMOTACTIC ACTIVITY OF WOUND FLUID WITH RECOMBINANT PDGF BB HOMODIMER

| Factor | | Stimulation of cell migration, |
|---|---|---|
| Lower chamber | Upper Chamber | -fold |
| PDGF BB (10 ng/ml) | None | 3.7 |
| Affinity-purified day-1 wound fluid | None | 3.8 |
| PDGF BB (10 ng/ml) | PDGF BB (25 ng/ml) | 0.9 |
| Affinity-purified day-1 wound fluid | PDGF BB | 0.9 |
| PDGF BB (10 ng/ml) | EGF (25 ng/ml) | 3.5 |
| PDGF BB (10 ng/ml) | FGF (25 ng/ml) | 3.3 |
| PDGF BB (10 ng/ml) | TGF-β (25 ng/ml) | 3.9 |
| None | None | 1.0 |

Chemotaxis was assayed as described. Neutralization of the positive PDGF or wound-fluid factor concentration gradient toward the lower chamber by adding PDGF to the upper chamber blocked the cell migration to the lower chamber. Other growth factors including epidermal growth factor (EGF), acidic fibroblast growth factor (FGF), and TGF-β at concentrations to 25 ng/ml did not block migration of the cells to PDGF.

TABLE 2

Homology of Gro Gene Product with LDGF

```
M A R A A L S  A A P S N P R L L R V A L L L L L L V A A G R R A A G A S  V A - - - - - - - - - - - T E    40
: :    .    : : :          :           .              . :                          :
M S L R L D T T P S C N S A R P L H A L Q V L L L L S L L L T A L A S S T K G Q T K R N L A K G K E E S L D S D L Y A E  60
```

TABLE 2-continued

Homology of Gro Gene Product with LDGF

```
L R C Q C L Q T L Q G I  HP KNI  QS VNVKS P GP HCAQTE VI  ATL KNG R KACL NP AS P I  VKKI  I  E KM    100
: : :  : .   :        : : : : : : : : : .  :         :      :     :    : : : : : : :    : : :   : :   :     :    . : : : .   :
L R C MCI  KT T S GI  HP KNI  QS L E VI  GKGT HCNQVE VI  ATL KDGR KI  CL DP DAP R I  KKI  VQKK    120

L N S D K S N                                            107
:    :     :
L A G D E S A D                                          128
```

Aligned 119, Matches 48, Mismatches 71, Homology 40%

TABLE 3

Homology of PDGF B-Chain Mature Protein with LDGF

```
   S L GS L T I  AEP AMI  AE CKT RT E VF E I  S RR L I  DRT NANF L VWP P C VE VQR C S GC CNNR NL QC    60
                                                                 :  :            :       .                :
                                                      MS L RL DT T P S CNS ARP L HAL QVL L L L S L       28

R P T QVQL R P VQVR KI  E I  VR KKP I  F KKAT VT L E DHL AC KC - E T VAAAR P VT                      109
:  .                   :            .  :                  :            :  :  :     :    .        :
L L T AL AS S T KGQT KR NL AKGKE E S L DS - - DL YAE L R CMCI  KT T S GI  HP KNI  QS L E VI  GKG     86

T HCNQVE VI  ATL KDGR KI  CL DP DAP R I  KKI  VQKKL AGDE S AD                                       128
```

Aligned 78, Matches 12, Mismatches 66, Homology 15%

I claim:

1. A method of facilitating the healing of a wound, comprising: treating the wound with a chemotactically or mitogenically effective amount of a purified leukocyte-derived growth factor comprising the amino acid sequence depicted in FIG. 1 such that facilitation of the healing of the wound occurs.

2. A method of facilitating the healing of a wound, comprising: treating the wound with a chemotactically or mitogenically effective amount of a purified mutant leukocyte-derived growth factor comprising an amino acid sequence that differs from that depicted in FIG. 1 by one or more conservative amino acid substitutions of an amino acid in FIG. 1 for a different amino acid of the same exchange group, such that the mutant retains the chemotactic or mitogenic activity of the leukocyte-derived growth factor having the amino acid sequence of FIG. 1.

3. The method of claim 2, wherein said leukocyte-derived growth factor is a mutant characterized by one or more conservative substitutions of a different amino acid of the same group, as hereafter defined, for an amino acid in the amino acid sequence of FIG. 1, said substitutions being selected from the group consisting of (A) Ala, Gly; (B) Asp, Glu; (C) Phe, Tyr; (D) Ile, Leu, Val; (E) Lys, Arg; (F) Asn, Gln; and (G) Ser, Thr, such that the mutant retains the chemotactic or mitogenic activity of the leukocyte-derived growth factor having the amino acid sequence of FIG. 1.

4. The method of claim 3, wherein said substitutions in the mutant are selected from at least one of the group consisting of threonine for serine 35; threonine for serine 36; and glutamine for asparagine 44.

5. The method of claim 2, wherein the mutant leukocyte-derived growth factor differs from native leukocyte-derived growth factor at least by the modification of a protease cleavage site so as to render the mutant leukocyte-derived growth factor less susceptible to proteolytic degradation than native leukocyte-derived growth factor.

6. The method of claim 2, wherein said exchange group is Phe, Tyr, Trp.

7. The method of claim 2, wherein said exchange group is Lys, Arg, His.

8. The method of claim 2, wherein said exchange group is Val, Leu, Ile, Met, Cys.

9. The method of claim 2, wherein said exchange group is Ser, Thr, Asp, Asn, Gly, Ala, Glu, Gln, Pro.

10. A method of facilitating the healing of a wound, comprising: treating the wound with a chemotactically or mitogenically effective amount of a purified leukocyte-derived growth factor having the amino acid sequence depicted in FIG. 1 such that facilitation of the healing of the wound occurs.

11. A wound healing composition comprising a chemotactically or mitogenically effective amount of a purified leukocyte-derived growth factor consisting of the amino acid sequence depicted in FIG. 1 and a pharmaceutically acceptable carrier.

12. A wound healing composition comprising a chemotactically or mitogenically effective amount of a purified leukocyte-derived growth factor which is a mutant characterized by one or more conservative substitutions of an amino acid in FIG. 1 for a different amino acid of the same exchange group and a pharmaceutically acceptable carrier, such that the mutant retains the chemotactic or mitogenic activity of the leukocyte-derived growth factor having the amino acid sequence of FIG. 1.

13. A method of facilitating the healing of a wound, comprising: treating a wound with a chemotactically or mitogenically effective amount of a purified mutant leukocyte-derived growth factor comprising an amino acid sequence that differs from that depicted in FIG. 1 by modification of a protease cleavage site within the amino acid sequence which renders the mutant leukocyte-derived growth factor less susceptible to proteolytic degradation than native leukocyte-derived growth factor, such that the mutant retains the chemotactic or mitogenic activity of the leukocyte-derived growth factor having the amino acid sequence of FIG. 1 and facilitation of healing of the wound occurs.

* * * * *